US008791082B2

(12) United States Patent
Rossi et al.

(10) Patent No.: US 8,791,082 B2
(45) Date of Patent: Jul. 29, 2014

(54) DOUBLE-STRANDED AND SINGLE-STRANDED RNA MOLECULES WITH 5' TRIPHOSPHATES AND THEIR USE FOR INDUCING INTERFERON

(75) Inventors: John J. Rossi, Alta Loma, CA (US); Dongho Kim, Los Angeles, CA (US); Patric Lundberg, Rancho Cucamonga, CA (US); Edouard Cantin, Alhambra, CA (US)

(73) Assignee: City of Hope, Duarte, CA (US)

( * ) Notice: Subject to any disclaimer, the term of this patent is extended or adjusted under 35 U.S.C. 154(b) by 1364 days.

(21) Appl. No.: 11/859,306

(22) Filed: Sep. 21, 2007

(65) Prior Publication Data

US 2008/0153162 A1 Jun. 26, 2008

Related U.S. Application Data

(62) Division of application No. 11/347,833, filed on Feb. 6, 2006, now abandoned.

(60) Provisional application No. 60/649,537, filed on Feb. 4, 2005.

(51) Int. Cl.
*C12N 15/113* (2010.01)
*C07H 21/04* (2006.01)

(52) U.S. Cl.
CPC .................................. *C12N 15/113* (2013.01)
USPC ....................................... 514/44 A; 536/24.5

(58) Field of Classification Search
None
See application file for complete search history.

(56) References Cited

U.S. PATENT DOCUMENTS

2004/0086884 A1* 5/2004 Beach et al. ...................... 435/6

OTHER PUBLICATIONS

Sambrook et al. Molecular Cloning, a Laboratory Manual, 2nd edition, Cold Spring Harbor Laboratory Press, 1989. pp. 5.58-5.59.*
Jacque et al. Nature 2002 vol. 418, pp. 435-438.*
Andino, R. RNAi puts a lid on virus replication. *Nat. Biotechnol.* 21, 629-630 (2003).

Beutler, B. Inferences, questions and possibilities in Toll-like receptor signaling. *Nature* 430, 257-63 (2004a).
Beutler, B. Inferences, questions and possibilities in Toll-like receptor signaling. *Nature* 430, 257-63 (2004b).
Boehme, K.W. and Compton, T. Innate sensing of viruses by toll-like receptors. *J Virol* 78, 7867-73 (2004).
Bridge, A.J., et al., Induction of an interferon response by RNAi vectors in mammalian cells. *Nature*, 34(3), 263-264 (2003).
Diebold, S.S., et al. Innate antiviral responses by means of TLR7-mediated recognition of single-stranded RNA. *Science* 303, 1529-31 (2004).
Donze, O. and Picard, D. RNA interference in mammalian cells using siRNAs synthesized with T7 RNA polymerase. *Nucleic Acids Res.* 30, e46 (2002).
Elbashir, S.M., et al. Duplexes of 21-nucleotide RNAs mediate RNA interference in cultured mammalian cells. *Nature* 411, 494-498 (2001).
Hannon, G.J. RNA interference. *Nature* 418, 244-251 (2002).
Heil, F. et al. Species-specific recognition of single-stranded RNA via toll-like receptor 7 and 8. *Science* 303, 1526-9 (2004).
Hornung, V. et al. Sequence-specific potent induction of IFN-alpha by short interfering RNA in plasmacytoid dendritic cells through TLR7. *Nat Med* 11, 263-70 (2005).
Lund, J.M. et al. Recognition of single-stranded RNA viruses by Toll-like receptor 7. *Proc Natl Acad Sci U S A* 101, 5598-603 (2004).
Malmgaard, L. Induction and regulation of IFNs during viral infections. *J Interferon Cytokine Res* 24, 439-54 (2004).
Samuel, C.E. Antiviral actions of interferons. *Clin. Microbiol. Rev.* 14, 778-809 (2001).
Sledz, C.A., et al. Activation of the interferon system by short-interfering RNAs. *Nature Cell Biology*, 5(9), 834-39 (2003).
Sohail, M., et al. A simple and cost-effective method for producing small interfering RNAs with high efficacy. *Nucleic Acids Res.* 31, e38 (2003).
Kim, D.H. et al., "Interferon induction by siRNAs and SSRNAs synthesized by phage polymerase", Nature Biotechnology, 22:3, 321-325 (Mar. 2004).
Alexopoulou, L., "Recognition of double-stranded RNA and activation of NF-κB by Toll-like receptor 3", Nature, vol. 413, Oct. 18, 2001, pp. 732-738.

* cited by examiner

*Primary Examiner* — Tracy Vivlemore
(74) *Attorney, Agent, or Firm* — Rothwell, Figg, Ernst & Manbeck P.C.

(57) ABSTRACT

Double-stranded and single-stranded RNA molecules, and their use in methods for inducing interferon are provided. The interferon induction provides anti-viral and other medically useful effects, such as anti-cancer effects. Also provided are methods for reducing or inhibiting interferon induction exhibited by such molecules, particularly siRNA and shRNA molecules produced in vitro.

3 Claims, 34 Drawing Sheets

5' UTR OF EMCV VIRAL GENOME 1 ttgaaagccg ggggtgggag atccggattg ccagtctact cgatatcgca ggctgggtcc
                             siRNA 1                          siRNA 2 gtgactaccc actcctactt tcaacgtgaa ggctacgata gtgccagggc gggtactgcc 120
                                                            siRNA 3

FIG. 6

GFP#2 synthetic I     5´OH-GCUGACCCUGAAGUUCAUCUU
                                    UUCGACUGGGACUUCAAGUAGOH-5´

GFP#2 synthetic II     5´OHGGGGCUGACCCUGAAGUUCAUCUU
                                    UUCGACUGGGACUUCAAGUAGGGGOH5´

GFP#2 T7     5´pppGGGGCUGACCCUGAAGUUCAUCUU
                                    UUCGACUGGGACUUCAAGUAGGGGPPP5´

GFP#2 T7 (19-AA)     5´pppGGGGCUGACCCUGAAGUUCAUCAA
                                    AACGACUGGGACUUCAAGUAGGGGPPP5´

GFP#2 T7 (21-AA)     5´pppGGGAAGCUGACCCUGAAGUUCAUCAA
                                    AAUUCGACUGGGACUUCAAGUAGGGGPPP5´

FIG. 7A

Mock vs T7
Mock vs Polyic

Mus musculus, clone IMAGE: 3590001, mRNA, partial cds
Interferon activated gene 202A
RIKEN cDNA 2310076014 gene
RIKEN cDNA 9130017N09 gene
Zinc finger protein 147
Siogren syndrome antigen A1
Myxovirus (influenza virus) resistance 2
Mus musculus myxovirus (influenza virus) resistance 1 (Mx1), mRNA
Mus musculus (strain C57B1/6) mRNA sequence
Interferon inducible protein 1
Interferon dependent positive acting transcription factor 3 gamma
Interferon activated gene 204
RIKEN cDNA 1700027J05 gene
Mus musculus small inducible cytokine A5 (Scya5), mRNA
FBJ osteosarcoma oncogene
ATP-binding cassette, sub-family B (MDR/TAP), member 2
Interleukin 15
Interferon-g induced GTPase
RIKEN cDNA 1700121D12 gene
T-cell specific GTPase
RIKEN cDNA 5830458K16 gene
Mus musculus guanylate nucleotide binding protein 3 (Gbp3), mRNA
Interferon gamma induced GTPase
Mus musculus CC1 mRNA for coiled-coil protein, complete cds
Mus musculus adult male hippocampus cDNA, RIKEN full-length enriched library, clone:2900034J12, full insert sequence
Guanylate nucleotide binding protein 3
Fas death domain-associated protein
Ubiquitin specific protease 18
Mus musculus T-cell specific GTPase (Tgtp), mRNA
Interferon-inducible GTPase
Interferon-induced protein with tetratricopeptide repeats 3
Interferon alpha responsive gene, 15 kDa
Hypothetical protein, MGC: 7868
RIKEN cDNA 1810027I20 gene
Guanylate nucleotide binding protein 1
DNA segment, Chr 11, KL Mohlke 35
Mus musculus interferon-induced protein with tetratricopeptide repeats 3 (Ifit3), mRNA
Interferon-stimulated protein (15 kDa)
Interferon-induced protein with tetratricopeptide repeats 1

FIG. 13A

| Mock vs T7
| Mock vs Poly IC

Myxovirus (influenza virus) resistance 1
Eukaryotic translation initiation factor 2 alpha kinase 2
Interferon regulatory factor 7
DNA segment, Chr 11, Lothar Hennighausen 2, expressed
Mus musculus guanylate nucleotide binding protein 1 (Gbp1), mRNA
Interferon gamma inducible protein, 47 kDa
RIKEN cDNA 2310047A08 gene
RIKEN cDNA 1500032H18 gene
Regulatory protein, T lymphocyte 1
Mus musculus mRNA for microtubule associated protein 44 (Mtap44 gene)
Guanylate nucleotide binding protein 2
Mus musculus 54 kDa oligoadenylate synthetase-like protein p540ASL mRNA, complete cds
RIKEN cDNA 5830443L24 gene
Signal transducer and activator of transcription 1
Mus musculus toll-like receptor 3 (Tlr3) mRNA, complete cds
Torsin family 3, member A
RIKEN cDNA 2010008K16 gene
Nuclear antigen Sp100
Mus musculus macrophage activation 2 (Mpa2), mRNA
Mouse 2'-5' oligo A synthetase mRNA, complete cds
RIKEN cDNA 1110004C05 gene
Petidylprolyl isomerase C-associated protein

FIG. 13B

☐ Mock vs T7
☐ Mock vs PolyIC

Oncostatin receptor
Mus musculus oncostatin receptor (Osmr), mRNA
Vascular cell adhesion molecule 1
RIKEN cDNA 2610022J01 gene
Mus musculus cytokine inducible SH2-containing protein 1 (Cish1), mRNA
Histocompatibility 2.0 region locus 7
Mouse cytokine (fic) mRNA, complete cds
Interleukin 6
Tachykinin receptor 2
oncostatin receptor
Immunoresponsive gene 1
Mouse MHC class I 08/9d cell surface antigen mRNA, complete cds
Heme oxygnease (decycling) 1
Sterol 0-acyltransferase 2
Myelocytomatosis oncogene
Mus musculus histocompatibility 2, Q region locus 5 (H2-Q5), mRNA
Jun-B oncogene
Interferon alpha family, gene 4
Mus musculus butyrate response factor 2 (Brf2), mRNA
Kruppel-like factor 2 (lung)
Heparin binding epidermal growth factor-like growth factor
GTP binding protein (gene overexpressed in skeletal muscle)
Glial cell line derived neurotrophic factor
Complement component 9
Stanniocalcin 2
Early growth response 1
Ankyrin-like repeat protein
Small inducible cytokine A4
RIKEN cDNA 4933438A12 gene
RIKEN cDNA 2810003M17 gene
Prolactin-like protein G
Nedd4 WW-binding protein 4
Myeloid differentiation primary response gene 116
Mus musculus tumor necrosis factor, alpha-induced protein 3 (Tnfaip3), mRNA
RIKEN cDNA 1810008K03 gene
Pentaxin related gene
Histocompatibility 2, 0 region locus 5
Growth arrest and DNA-damage-inducible, alpha
Mus musculus growth arrest and DNA-damage-inducible, alpha (Gadd45a), mRNA

FIG. 14A

Mock vs T7
Mock vs Poly IC

Histone H1
Growth arrest and DNA-damage-inducible, gamma
ENV POLYPROTEIN PRECURSOR
RIKEN cDNA 2310004N11 gene
RIKEN cDNA 1500031O19 gene
Myeloid differentiation primary response gene 118
Mus musculus Lv6/neurotoxin 1 (Lynx1), mRNA
SH3 domain protein 5
RIKEN cDNA 5830405C08 gene
RIKEN cDNA 1200003C15 gene
Mus musculus myeloid differentiation primary response gene 118 (Myd118), mRNA
Latent transforming growth factor beta binding protein 2
Interferon alpha family, gene B
Immediate early response 2
Thymic stromal lymphopoietin
Thrombospondin 1
RIKEN cDNA 5930426I11 gene
RIKEN cDNA 4930425B13 gene
Mus musculus genomic DNA sequence from clone 573K1 on chromosome 17. Contains the gene for gamma-ami
Keratin complex 1, acidic, gene 16
Inhibin beta-A
Core promoter element binding protein
RIKEN cDNA 1700012B07 gene
RIKEN cDNA 1110070A02 gene
Procollagen, type V, alpha 3
Nuclear factor of kappa light polypeptide gene enhancer in B-cells inhibitor, epsilon
Adenosine deaminase, RNA-specific
Actin, alpha 1, skeletal muscle
Ski/sno related
RIKEN cDNA 4631422O05 gene
RIKEN cDNA 1810032O08 gene
RIKEN cDNA 1500003K04 gene
Interferon alpha family, gene 5
Early growth response 2
calcium channel, voltage-dependent, alpha 2/delta subunit 2

FIG. 14B

Mock vs T7
Mock vs PolyIC
T7 vs PolyIC

Prolactin-like protein G
Mus musculus tyrosine 3-monoxygenase/tryptophan 5-monooxygenase activation protein, zeta polypeptide (Ywhaz), mRNA
Prostaglandin-endoperoxide synthase 2
Human immunodeficiency virus type I enhancer-binding protein 2
H3 histone, family 2
RIKEN cDNA 1200008D14 gene
Mus musculus mRNA for limitin, complete cds
RIKEN cDNA 1700012B07 gene
Mus musculus genomic DNA sequence from clone 573K1 on chromosome 17. Contains the gene for gamma-ami
RIKEN cDNA 1810013L24 gene
Retinol dehydrogenase type 5
Transgelin
Small inducible cytokine subfamily, member 2
RIKEN cDNA 1810045C04 gene
RIKEN cDNA 1500011J06 gene
S100 calcium binding protein A3
RIKEN cDNA 3110043021 gene
Ecotropic viral integration site 1
Antigen identified by monoclonal antibodies 4F2
Nuclear factor of kappa light polypeptide gene enhancer in B-cells inhibitor, epsilon
Mus musculus proviral integration site 1 (Pim1), mRNA
Core promoter element binding protein
Avian reticuloendotheliosis viral (v-rel) oncogene homolog A
Inhibin beta-A
Cyclin ania-6a

FIG. 14C

Cyclin ania-6a
RIKEN cDNA 4930425B13 gene
RIKEN cDNA 2310026P19 gene
Procollagen, type V, alpha 3
Immediate early response 2
Actin, alpha 1, skeletal muscle
Mus musculus myeloid differentiation primary response gene 118 (Myd118), mRNA
Mus musculus cyclin ania-6a (LOC56706), mRNA
Mus musculus adult male tongue cDNA, RIKEN full-length enriched library, clone:2310067E17, full insert sequence
Early growth response 2
Thrombospondin 1
RIKEN cDNA 5930426I11 gene
RIKEN cDNA 2700038I16 gene
RIKEN cDNA 1700020E22 gene
Mus musculus butyrate response factor 1 (Brf1), mRNA
Latent transforming growth factor beta binding protein 2
RIKEN cDNA 150000K04 gene
Protein associated with Lin-7
Ski/sno related
Mus musculus, Similar to hypothetical protein, clone MGC:11704, mRNA, complete cds
FBJ osteosarcoma oncogene B
Troponin T2, cardiac
Tumor necrosis factor, alpha-induced protein 3
Mus musculus small inducible cytokine A4 (Scya4), mRNA
Regulator of G-protein signaling 16
Prolactin-like protein E
Mus musculus dystonin (Bpag1-n) mRNA, partial cds
B-cell leukemia/lymphoma 3

FIG. 14D

DOUBLE-STRANDED AND SINGLE-STRANDED RNA MOLECULES WITH 5' TRIPHOSPHATES AND THEIR USE FOR INDUCING INTERFERON

CROSS-REFERENCE TO RELATED APPLICATION

The present application is a division of U.S. patent application Ser. No. 11/347,833 filed on 6 Feb. 2006 which in turn is related to and claims priority under 35 U.S.C. §119(e) to U.S. provisional patent application Ser. No. 60/649,537 filed on 4 Feb. 2005. Each application is incorporated herein by reference.

The invention described herein was made with Government support under grant number HL074704 from NHLBI of the National Institutes of Health. Accordingly, the United States Government may have certain rights in this invention.

FIELD OF THE INVENTION

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The present invention relates to RNA molecules, including double-stranded and single-stranded RNA molecules, and their use for inducing interferon. The present invention also relates to methods for controlling interferon induction by such molecules.

BACKGROUND OF THE INVENTION

Small interfering RNAs (siRNA) are potent reagents for directed post-transcriptional gene silencing (Hannon, G. J., 2002). siRNAs are double-stranded molecules typically 21 to 25 nucleotides (nt) in length, which trigger RNA interference (RNAi), resulting in post-transcriptional message degradation (Elbashir, S. M., et al., 2001) and inhibition of viral propagation (Andino, R., 2003). RNAi has emerged as an immensely important and popular method to elicit post-transcriptional, sequence-specific silencing of gene expression and is a major new genetic tool for investigating mammalian cells. RNAi is initiated by exposing cells to dsRNA either via transfection or endogenous expression. Long double-stranded (ds) RNAs are processed into siRNAs by dicer, a ribonuclease of the Rnase III family. These siRNAs form a complex known as the RNA Induced Silencing Complex or RISC, which functions in homologous target RNA destruction (Montgomery, M. K., 2004).

The use of exogenously supplied siRNAs for targeted RNA knockdowns has become widespread (Elbashir, S. M., et al., 2001). The exogenous RNAs can be manufactured synthetically. However, when synthetic siRNAs are used for gene silencing, the costs can be substantial because of variations in siRNA efficacies. An alternative to chemically synthesized siRNAs are siRNAs produced by bacteriophage T7 RNA polymerase. These siRNAs are made by in vitro transcription mediated by bacteriophage promoters from linearized DNA templates. In vitro transcription using bacteriophage T7 RNA polymerase has been shown to produce highly active siRNAs (Sohail, M., et al., 2003; Donze, O. and Picard, D., 2002).

The interferon (IFN) system is one of the body's first lines of defense against viruses (Samuel, C. E., 2004). IFN was discovered as an antiviral agent by Isaacs and Lindenmann during studies on virus interference, where they observed that cells infected with influenza virus secrete a factor that mediates the transfer of a virus-resistant state active against both the inducing virus and other viruses as well (Samuel, C. E., 2004). Double-stranded RNA (dsRNA) is known to play an important role in the IFN system (Samuel, C. E., 2001). It is known that synthetic dsRNAs and RNAs with double-stranded character produced during viral infections have the capacity to be potent inducers of IFN (Stewart, W. E., 1979; Marcus, P. I., 1983).

The early recognition of invasive pathogens by innate sensing is the most important defense mechanism of the immune system (Beutler, B., 2004a; Boehme, K. W. and Compton, T., 2004). Viral infection of mammalian cells results in activation of an innate immune response which is mediated by interferons and cytokines that concomitantly inhibit viral replication (Malmgaard, L., 2004). Several Toll-Like Receptors (TLRs) have been identified in humans and mice and are known to be expressed predominantly on cell types which are first to encounter intracellular pathogens (Boehme, K. W. and Compton, T., 2004). Double stranded RNA (dsRNA), including the synthetic analog poly inosine-poly cytosine (Poly IC), is known to activate TLR3, a cellular receptor that recognizes and initiates a potent anti-viral response by producing interferons (Alexopoulou, L., et al., 2001). Similarly, single stranded RNA (ssRNA), which includes the genomes of several viral RNA species, has been shown to interact with and activate TLR7 and TLR8 (Lund, J. M., et al., 2004; Diebold, S. S., et al., 2004; Heil, F., et al., 2004; Hornung, V., et al., 2005). dsRNAs can be easily distinguished intracellularly as viral replication intermediates, however, it remains elusive how a simple ssRNA motif recognized by TLR7 and 8 is discerned by the cell to be either viral (exogenous) or endogenous in origin (Boehme, K. W. and Compton, T., 2004). Considering that TLRs are cell type specific and are present within unique localized intracellular compartments, recognition of dsRNA and/or ssRNA offers an important innate defense mechanism against viral infection along with the recognition of CpG DNA motifs and/or envelope glycoproteins (Boehme, K. W. and Compton, T., 2004; Beutler, B., 2004b)

RNAi-mediated gene silencing in mammalian cells requires siRNAs of sufficiently small size to circumvent potential sequence-independent, nonspecific changes in gene expression attributable to the induction or action of interferons. Sledz, C. A., et al. (2003) found that transfection of siRNAs results in interferon (IFN)-mediated activation of the Jak-Stat pathway and global upregulation of IFN-stimulated genes. The authors showed that by using cell lines deficient in specific components mediating IFN action that the RNAi mechanism itself is independent of the interferon system. The authors characterized their finding as showing the "broad and complicating effects" of siRNAs beyond the selective silencing of target genes when introduced into cells. Similarly, Bridge, A. J., et al. (2003) reported that although siRNAs were thought to be too short to induce interferon expression, a commonly used shRNA construct was found to induce an interferon response. The authors advise as a "simple precaution to limit the risk of inducing an interferon response" to use the lowest effective dose of shRNA vector.

Although the anti-viral activities of interferons are well studied (Samuel, C. E., 2001), nobody has recognized in connection with RNAi the uses and advantages, as opposed to the risks, of interferon induction by RNAi molecules, independent of the RNAi effect, to provide anti-viral and other effects, such as anti-cancer effects. Moreover, until now, nobody is believed to have discovered the role of the triphosphate, in particular the 5-triphosphate produced on RNAi molecules in vitro, for inducing interferon and eliciting antiviral and other medically useful responses.

SUMMARY OF THE INVENTION

The present invention is believed to be first to show that the presence of an initiating triphosphate on in vitro transcribed-RNAs can potently induce interferon α and β, as well as elicit a strong, non-sequence-specific antiviral response to viral challenge.

The present invention relates in one aspect to double-stranded RNA molecules, including RNAi molecules, and in another aspect to single-stranded RNA molecules, on which one or more triphosphates, preferably one or more 5'-triphosphates, are maintained in order to exploit the interferon induction properties of such molecules, in order to provide anti-viral and other medically useful (e.g., anti-cancer) effects.

The present invention relates in one embodiment to a method for inducing interferon in a cell, comprising exposing or introducing into the cell an effective amount of an RNAi molecule having one or more triphosphates, preferably a 5'-triphosphate, wherein said RNAi molecule induces said interferon. The RNAi molecule also can have an anti-viral effect, and preferably, is introduced into the cell prior to viral infection, wherein the RNAi molecule inhibits or prevents viral infection. The RNAi molecule also can have other medically useful effects, such as an anti-cancer effect.

In another embodiment, the invention provides a composition for inducing interferon in a cell comprising an effective amount of an RNAi molecule having one or more triphosphates, preferably a 5'-triphosphate, wherein the RNAi molecule can induce interferon in the cell. In a preferred embodiment, the RNAi molecule can also have an anti-viral or anti-cancer effect.

In another embodiment, the invention provides an antiviral reagent comprising an effective amount of an RNAi molecule having one or more triphosphates, preferably a 5'-triphosphate, wherein the RNAi molecule in addition to inducing interferon also has an anti-viral effect. In one embodiment, the anti-viral effect is the result of interferon induced by the RNAi molecule in a non-sequence dependent manner. In another embodiment, the anti-viral effect is the result of a synergy between an RNAi effect mediated by the RNAi molecule (i.e., as a result of homology between the RNAi molecule and its target molecule) and an immune response mediated by interferon induction.

In another embodiment, the invention provides a method for inducing an anti-viral response in a cell, comprising introducing into a cell an effective amount of an RNAi molecule having one or more triphosphates, preferably a 5'-triphosphate, and which exhibits one of the above anti-viral effects.

The cell can be any cell and is preferably a eukaryotic or vertebrate cell, more preferably a mammalian cell, and most preferably a human cell.

In a preferred embodiment, the RNAi molecule is an siRNA or an shRNA.

In another aspect, the present invention provides a method for inducing interferon in a cell, comprising introducing into the cell an effective amount of a short single-stranded RNA (ssRNA) having one or more triphosphates, preferably a 5'-triphosphate, wherein the ssRNA molecule induces interferon, and preferably also has an anti-viral or other medically useful (e.g., anti-cancer) effect, as described above.

In a more preferred embodiment of each of the above embodiments, the RNAi molecule and ssRNA molecule are produced in vitro by a phage polymerase. In a preferred embodiment, the phage polymerase is T7 RNA polymerase, T3 RNA polymerase or Sp6 RNA polymerase. In an even more preferred embodiment, the polymerase is T7 RNA polymerase.

In the present invention, the 5'-triphosphate of an RNAi or ssRNA molecule produced in vitro has been discovered to be an active inducer of interferon, as well as a potent anti-viral agent. On the other hand, the present invention also recognizes advantages of removing the 5' triphosphate from in vitro transcribed RNAi molecules, and thus reducing or inhibiting interferon induction. This additional aspect of the invention should be useful for controlling, reducing or inhibiting interferon induced during gene silencing using such RNAi molecules.

In yet another aspect, the present invention thus provides an in vitro method for producing or synthesizing an RNAi molecule which reduces or alleviates the interferon response exhibited by a double-stranded, preferably an RNAi, molecule or ssRNA molecule produced in vitro, while maintaining the efficacy of the molecule. In one embodiment, the method comprises removing one or more 5'-triphosphates from the molecule, wherein the removal reduces or alleviates the interferon response while maintaining the efficacy of the molecule.

BRIEF DESCRIPTION OF THE FIGURES

FIG. 2A is a graph showing that the anti-HSV-1 activity is mediated by induction of interferon α and β. The anti-HSV-1 activity was assayed using the medium from siRNA-transfected cells. Either a single (col. 3 or 4) or both neutralizing antibodies (col. 5) were tested.

FIG. 2B is a graph showing anti-HSV-1 activity of T7-transcribed siRNAs in HEK-293, HeLa and CV1 cell lines. 20 nM of T7-transcribed siRNA was transfected into the three different cell lines and HSV-1 infection was monitored.

FIG. 2C are graphs showing that RNAi and interferon induction are independent phenomena. Two different siRNAs, one targeting a susceptible site and the other a nonsusceptible site in EGFP, were synthesized chemically or transcribed by T7RNA polymerase and tested for RNAi efficacy (top) and interferon induction (bottom). The RNAi assay represents the average of three independent assays. The interferon results are the average of two independent experiments.

FIG. 2D is a graph showing the potency of the RNA-mediated anti-HSV-1 activity. The inhibition of HSV-1 infection was tested after transfection using the indicated amounts of synthetic or T7-transcribed siRNAs. The average of two independent experiments is presented.

FIG. 6 is a schematic of the 5'UTR of a EMCV viral genome (SEQ ID NO: 1). Also shown are the regions where siRNAs, produced in accordance with the present invention, bind the EMCV viral genome.

FIGS. 7A-7C show the role of the initiating triphosphate in interferon induction.

FIG. 7A shows siRNAs synthesized in accordance with the invention. (i) The EGFP #2 synthetic I (SEQ ID NOs:2 and 3), chemically synthesized siRNA against the EGFP #2 site, EGFP #2 synthetic II; (ii) the EGFP #2 synthetic II (SEQ ID NOs:4 and 5) with 5' OH-GGG; (iii) the EGFP #2 T7 (SEQ ID NOs:4 and 5), T7 RNA polymerase-transcribed siRNA against EGFP #2 containing 5' pppGGG; (iv) the EGFP #2 T7 (19-AA) (SEQ ID NOs:6 and 7), the same as EGFP #2 T7 RNA polymerase-transcribed siRNA except for replacing the 3' UU with 3' AA; (v) the EGFP #2 T7 (21-AA) (SEQ ID NOs:8 and 9), T7 RNA polymerase-transcribed siRNA with 21 nt complementary to the EGFP #2 site but including the 3' AA. The potential cleavage site for RNAse T1 is boldface. The 3' AA replacing the 3' UU is in italics. The AA complementary to UU is underlined.

FIG. 7B are a graph and gel photograph showing triphosphate-mediated interferon induction [$\gamma$-$^{32}$P] GTP-labeled siRNAs were treated using each of the conditions described below and electrophoresed in a native gel (top). RNAs (1 μg) were electrophoresed in a 15% polyacrylamide gel and stained with ethidium bromide (middle). 20 nM of siRNAs was transfected into HEK-293 cells and assayed for interferon β (bottom panel). Column 1, the EGFP #2 T7 siRNA without T1 treatment; column 2, with T1 treatment; column 3, with T1 and CIP treatment. Column 4, EGFP #2 T7 (19-AA) siRNA without T1 treatment; column 5, with T1 digestion; column 6, with T1 and CIP treatment.

FIG. 7C is a graph showing that T7 siRNAs (21-AA) in accordance with the invention are effective in RNAi. HEK-293 cells were cotransfected with the EGFP reporter plasmid and each of the siRNAs. The percentages of EGFP expression relative to the non-siRNA-treated controls were used as the assay for RNAi. Each value is the average of two independent assays.

FIG. 8A is a graph showing that ssRNAs transcribed in vitro elicit the anti-HSV-1 effect. Mock 1: before transfection, the RNA sample was mixed with 1 μg of RNase A. Mock 2: transfection of RNA containing triphosphate done in the absence of a transfection reagent. T7 siRNA1 and 2 are the T7 siRNAs for HSV #1 and anti-SF3A3 #1, respectively. The T7 ssRNA is the sense RNA strand of HSV#1. The T7 EGFP was RNA-transcribed from an EGFP-encoding DNA template. T7 $(CUG)_{130}$ is a T7-transcribed RNA harboring 130 repeats of CUG. All RNAs were used at a concentration of 20 nM.

FIG. 8B is a graph showing the anti-HSV-1 activities of ssRNAs transcribed from T7, T3 and Sp6 polymerases. The templates of T3 ssRNA 1 and 2 were created from the pBluecript II SK vector digested with EcoRI and BamHI, respectively. The templates of SP6 ssRNA 1 and 2 were created by the EcoRI and SalI digestion of the pGEM 9Df(−) vector. The T7 ssRNA is the sense sequence of HSV #1.

FIG. 8C is a graph and gel photographs showing that the 5' triphosphate of the transcribed ssRNA is essential for the induction of interferon. The EGFP RNA was transcribed in the presence of [$\gamma$-32P]GTP and transfected into cells without any further modification (col. 2 and 3), after gel purification (col. 4 and 5), and after gel purification and CIP treatment (col. 6 and 7). The induced levels of interferon β were determined by an ELISA (top). Transcribed RNAs used for transfection reactions were analyzed in a nondenaturing agarose gel (middle). Removal of the triphosphate by CIP was monitored on the bottom gel. The ELISA determinations represent the average of two independent experiments.

FIG. 10A shows total RNA that was purified from influenza viral RNA and treated without (−CIP) or with (+CIP) calf intestinal phosphatase.

FIG. 10B shows HEK293 cells that were transfected with no RNA (mock), influenza viral RNA without CIP treatment (Flu RNA −CIP), or the RNA with CIP treatment (Flu RNA +CIP) and sequentially challenged by EGFP-labeled HSV. The infection of virus was monitored by florescence microscopy.

FIG. 10C shows HEK293 cells that were transfected with influenza viral RNAs without CIP pretreatment (second column) or with pretreatment at 10 (third) and 60 minutes (fourth column).

FIG. 10D shows NIH3T3 cells stably expressing EGFP that were treated with no RNA (mock), 1 nM of T7 RNA (T7 RNA), 0.5 ug of influenza viral RNA without CIP pre-treatment (Flu RNA-CIP), and the viral RNA with CIP pre-treatment (Flu RNA+CIP). The next day (24 hours), cells were challenged with EMCV infection. On day 3, the viral infection mediated cytotoxic effect was monitored under light (the first panel) or fluorescence microscopy (the second panel).

FIG. 11A shows cytoplasmic and nuclear extracts that were prepared from HEK293 cells and tested by Western blot for the cytoplasmic protein enolase or nuclear protein hnRNP H.

FIG. 11B shows cytoplasmic (the first lane) and nuclear RNAs (second and third lanes) that were purified from each extract and analyzed on a 1% agarose gel in the absence (second lane) or presence of CIP pre-treatment (third lane).

FIG. 11C shows HEK293 cells that were transfected with each indicated RNAs and sequentially infected with EGFP-labeled HSV. The pictures were taken under florescence microscopy on day 3.

FIG. 12A shows total cDNA from NIH3T3 cells transfected by the T7 RNA or poly IC that were detected and quantitated by microarray analysis. The expression profiles were compared between mock treated vs. T7 RNA (the first column), mock vs. poly IC (the second column), and T7 RNA vs. poly IC (the third column). The bar represents the total number of genes where were up or down-regulated by more than three-fold using a total of 16,281 elopements and an average of two independent trials.

FIG. 12B shows that TLR3 is upregulated by poly IC as well as by T7 RNA. Total RNA of NIH3T3 cells were harvested after transfection with no RNA, T7 RNA, and poly IC. Based on the microarray data in FIGS. 14A-14D, the expression level of TLR3 was compared. TLR7 and beta-actin were used as internal controls.

FIG. 12C shows that TLR3 is required for the T7 RNA mediated innate immune response. MRC-5 cells were pre-incubated in the presence of anti-TLR2 or TLR3 antibodies and incubated in the presence of the indicated RNAs. The secreted interferon beta in the media was determined by ELISA in three independent assays.

FIGS. 13A-13B show that all 86 genes upregulated by the T7 transcribed RNA were also upregulated by poly IC.

FIGS. 14A-14D show that poly IC activated a large number of additional genes in comparison to genes activated by T7 transcribed RNA.

DETAILED DESCRIPTION OF THE INVENTION

The ability to detect pathogenic invasion is the first line of defense in a cell and represents the most important task of the innate immune response. As shown herein, siRNAs transcribed by T7 RNA polymerase display a potent anti-viral effect that is dependent on the presence of a 5' triphosphate motif. We suggest that the innate immune response is activated by the recognition of this RNA motif. It is also shown herein that Influenza A viral RNA induces 5' triphophate dependent anti-viral activity through the activation of the interferon response pathway when transfected directly into cells. Nuclear-derived RNAs which include many uncapped small RNAs and ribosomal RNAs harboring a 5' triphosphate label also activate a strong interferon induction when transfected into cells. Alkaline phosphatase treatment of these RNAs eliminates this stimulation and cytoplasmic-derived RNAs, which are largely devoid of triphosphate, also fail to induce an interferon response. The 5' triphosphate containing RNAs appear to be recognized by and activateToll Like Receptor 3 (TLR3). Microarray and functional analyses indicate that 5'triphophate containing RNAs constitute a novel immunostimulatory motif which is highly effective at inducing IFN responses in leading to potent antiviral activity in a variety of cell lines.

An embodiment of the present invention provides a method for inducing an interferon response in a cell comprising introducing into the cell an effective amount of a double-stranded RNA molecule, preferably an interfering RNA (RNAi) molecule, having a triphosphate, preferably a 5'-triphosphate. The presence of the 5'-triphosphate was found to induce the interferon response. The invention also encompasses variations of the triphosphate which enable induction of effective amounts of interferon. In a preferred embodiment, the RNAi molecule having a triphosphate, and preferably a 5'-triphosphate, induces one or more of interferon α and β. It is understood that the expressions "having a triphosphate" or "having a 5'-triphosphate" encompass having one or more triphosphates or 5'-triphosphates.

Figure 4:
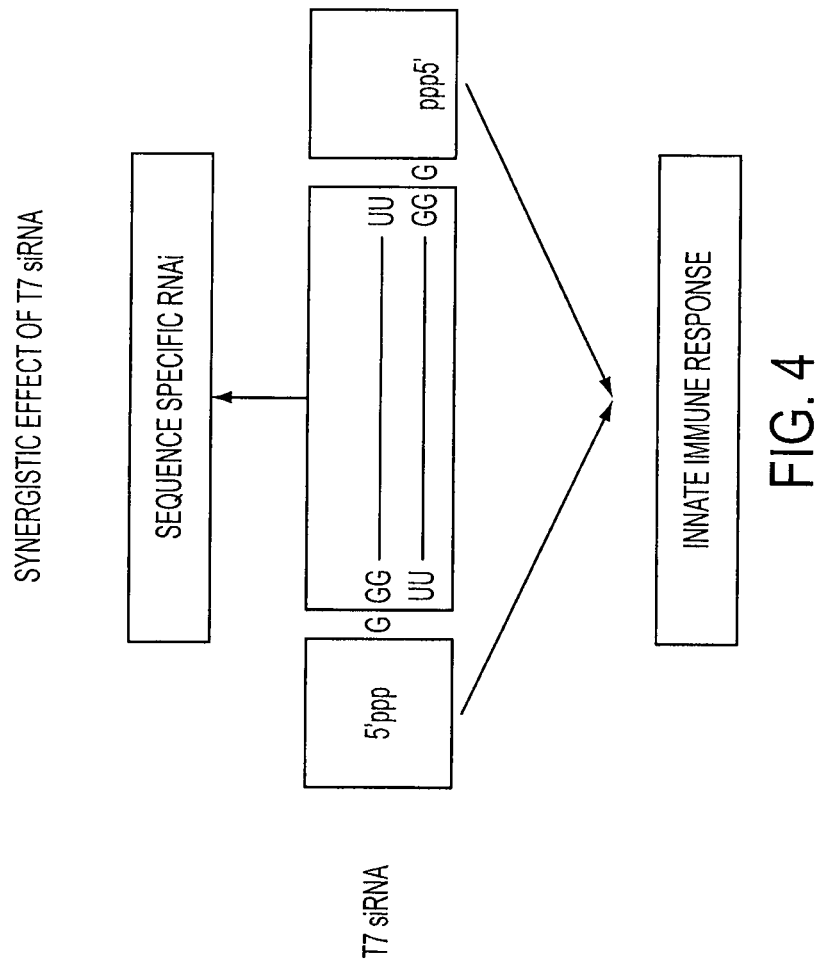
FIG. 4 is a schematic showing a T7 siRNA having a 5'-triphosphate produced in accordance with the present invention. The schematic shows the non-base paired nucleotide (G) to which the 5'triphosphate is attached. The schematic also shows the synergistic effects of the 5'-triphosphate mediated innate immune response and the siRNA mediated RNAi effect.

In a preferred embodiment, the double-stranded RNA, and preferably RNAi, molecule having a triphosphate, preferably a 5'-triphosphate, is produced in vitro by a phage polymerase, preferably a bacteriophage RNA polymerase. Preferably the nucleotide to which the triphosphate is attached is not base-paired to the opposite strand of the double-stranded molecule (FIG. 4). Preferably the RNAi molecule having a 5'-triphosphate is produced in vitro by a bacteriophage T7 RNA polymerase. In further embodiments of the invention, the RNAi molecule having a 5'-triphosphate may be produced by other phage polymerases, including a bacteriophage T3 RNA polymerase or a bacteriophage Sp6 RNA polymerase.

In another embodiment the double-stranded RNA, preferably RNAi, molecule having a triphosphate is synthetic or chemically synthesized.

The RNA molecules of the invention also can be purified using acceptable methods known in the art.

In a preferred embodiment, the RNAi molecule having a 5'-triphosphate is a small interfering RNA (siRNA). In another preferred embodiment, the RNAi molecule having a 5'-triphosphate is a short hairpin RNA (shRNA) molecule. The double-stranded RNA preferably has two triphosphates, and most preferably two 5'-triphosphates. The double-stranded RNA, preferably RNAi, and more preferably siRNA, molecule also is preferably about 10 to about 25 nucleotides in length, and more preferably about 20 nucleotides in length, while the shRNA, which can be used to produce a preferred siRNA, is preferably about 21 to about 29 nucleotides in length. In particular, it was found that triphosphate-containing double-stranded RNA as short as 10 nucleotides induced an interferon response. Longer RNA molecules were found to induce interferon as well, but the total concentration of the 5'-triphosphate is reduced. Therefore, the longer the RNA molecule, the more of the molecule is preferred, since the triphosphate is believed to effect interferon induction.

In another embodiment, the invention provides a composition for inducing an interferon response comprising an effective amount of an RNAi molecule having a triphosphate, preferably a 5'-triphosphate, wherein the presence of the 5'-triphosphate has been found to induce the interferon response.

In other embodiments, the invention provides an anti-viral reagent and a method for inducing an antiviral response, comprising introducing into a cell an effective amount of an RNAi molecule having a triphosphate, preferably a 5'-triphosphate, wherein the presence of the 5'-triphosphate induces an interferon response, and provides an anti-viral response. The anti-viral response can be mediated by interferons, or alternatively by both interferons and a sequence-dependent RNAi effect. The anti-viral response is not limited to mediation by interferons, but may include other cytokines or signaling pathways. In a preferred embodiment, the RNAi molecule having a 5'-triphosphate can be introduced into a cell prior to viral infection, thereby, inhibiting viral infection. The present invention is useful against any virus, including but not limited to, herpes simplex virus 1 (HSV-1), encephalomyocarditis virus (EMCV) or Influenza A virus.

The present invention can be practiced in vitro or in vivo. The invention also can be used as a therapeutic or preventative agent, preferably for therapy or prevention of a disease or condition.

An effective amount refers to that amount of RNA effective to produce the intended result, including the intended pharmacological, therapeutic or preventive result. In cell culture, an effective amount for initiating an antiviral effect can be as low as 1 nM, and can range up to 20 nM or more. However, it is understood that higher dosages can be toxic to cells, due to unregulated induction, resulting in undesired levels of expression of several cytokines, including interferon. A pharmaceutically effective amount or dose is that amount or dose required to prevent, inhibit the occurrence, or treat (alleviate a symptom to some extent, preferably all of the symptoms) of a disease state. The pharmaceutically effective amount or dose depends on the type of disease, the composition use, the route of administration, the type of mammal being treated, the physical characteristics of the specific mammal under consideration, concurrent medication, and other factors which those skilled in the medical arts will recognize. Generally, an effective amount or dose of dsRNA or ssRNA for human use is known in the art and/or can be determined by standard methods, and can be administered, for example, in the ranges of about 0.001 mg/kg to 100 mg/kg body weight/day or about 0.01 mg/kg to 10 mg/kg body weight/day.

Fire, A. et al. (2003), which is incorporated herein by reference, refers to introducing RNA in an amount which delivers at least one copy per cell, as well as administering higher dosages (e.g., 5, 10, 100, 500, 1000, etc., copies per cell) of double-stranded RNA to yield better results. Ackermann, E. J. et al. (1999), which is incorporated herein by reference, describes as follows: "The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$'s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years."

Methods for formulating compositions and reagents in accordance with the invention, as well as modes of administration, are known in the art and are described, for example, in Agrawal, S. et al. (2003) and Ackermann, E. J. et al. (1999), which are fully incorporated herein by reference. Formulations can include a pharmaceutically or physiologically acceptable carrier, such as an inert diluent or an assimilable edible carrier. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Methods for delivering the RNA molecules of the invention into cells also are well known in the art. See Thompson, J. et al. (2004) and Fire, A. et al. (2003), which are fully incorporated herein by reference. RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. Physical methods of introducing nucleic acids, for example, injection directly into the cell or extracellular injection into the organism, may also be used. Vascular or extravascular circulation, the blood or lymph system, the phloem, the roots, and the cerebrospinal fluid are sites where the RNA may be introduced.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

Methods for the delivery of nucleic acid molecules also are described in Akhtar and Juliano (1992) and Akhtar (1995), each of which is incorporated herein by reference. Sullivan et al. (1994) further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form), intrathecal, mucosal, or transdermal delivery. Other approaches include the use of various transport and carrier systems, for example, through the use of conjugates and biodegradable polymers. More detailed descriptions of nucleic acid delivery and administration are provided in Sullivan et al. (1994), Draper et al. (1993), Beigelman et al. (1999) and Klimuk et al. (1999), all of which are incorporated by reference herein.

Figure 1A:
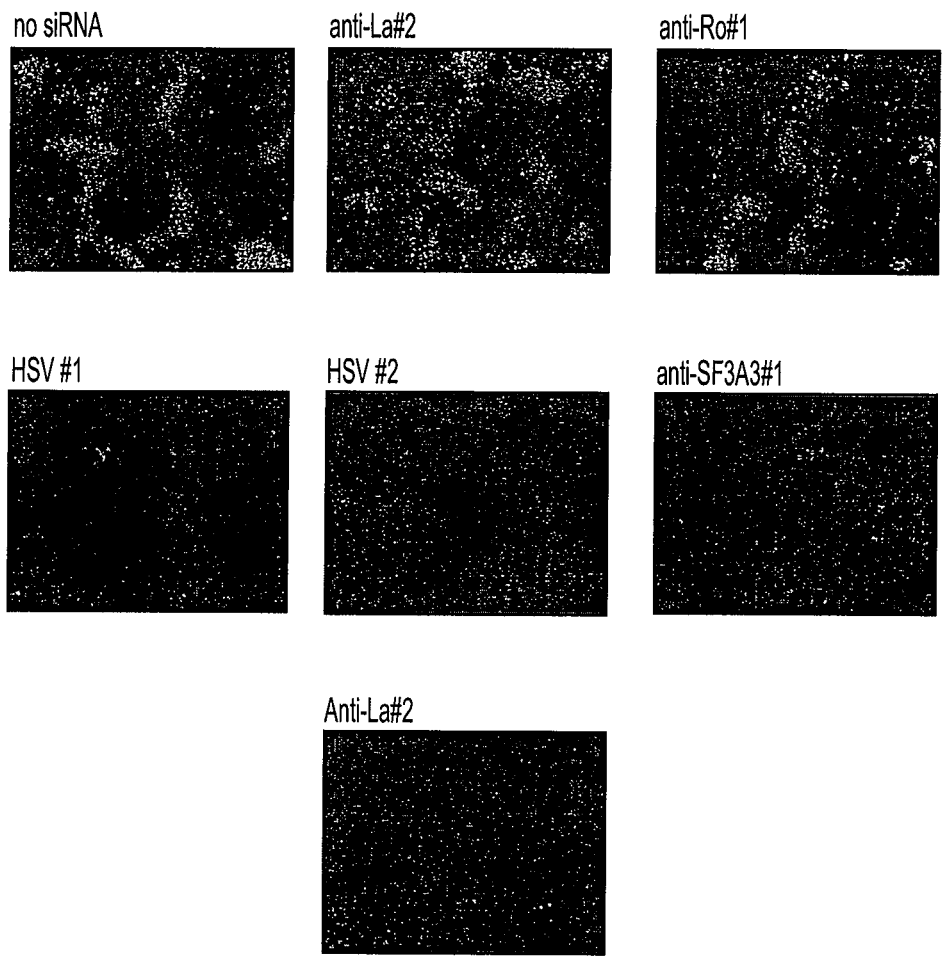
FIG. 1A are photographs showing anti-HSV-1 activities of T7 transcribed siRNAs. The siRNA transfected HEK-293 cells were infected with HSV-1-EGFP. Top panel, mock or chemically synthesized siRNA transfected samples (anti-La#2 and anti-Ro #1); middle panel, T7 siRNA transfected samples; lower panel, the anti-La #2 siRNAs were prepared by T7 RNA polymerase using the Silencer siRNA Construction Kit (Ambion).

In accordance with the present invention, interferon induction and anti-viral activity can be induced in response to a variety of RNAi molecules. To test for interferon induction and antiviral activity of an RNAi molecule, first, RNA interference was tested in one embodiment as a method to block herpes simplex virus 1 (HSV-1) infection. To perform this test, two siRNAs targeting the early ICP4 gene transcript were created using T7 RNA polymerase. The sequences of these are provided in Table 1. To monitor viral infection, an HSV-1 recombinant that contains the gene encoding VP20 fused to the gene encoding the enhanced green fluorescent protein (EGFP) was used (Elliott, G. and O'Hare, P., 1999). When cells are infected with the virus, they express EGFP, allowing simple microscopic assays for viral infectivity. First, human embryonic kidney (HEK) 293 cells were transfected with the siRNAs (10 nM each) before viral infection. Twenty hours later the recombinant HSV-EGFP virus was added to the cultured cells at a multiplicity of infection (MOI) of 1. Twenty-four hours after viral challenge, infectivity was monitored by microscopic analysis of EGFP expression. The two siRNAs targeting HSV-1 as well as one of the irrelevant siRNA controls inhibited viral infectivity dramatically (FIG. 1A). When analyzing the results of these experiments a correlation was found between the anti-HSV-1 activity and the source of the siRNAs. Whereas the two chemically synthesized siRNAs showed no anti-HSV-1 activity, all three of the siRNAs prepared by in vitro transcription using T7 RNA polymerase showed potent HSV-1 inhibition. Next, an siRNA with a sequence identical to the chemically synthesized control siRNA, the RNA binding protein La (Table 1), which did not have antiviral activity, was transcribed using a T7 RNA polymerase. The T7 RNA polymerase-transcribed version of this siRNA elicited a potent anti-HSV-1 response, supporting the hypothesis that some component of the T7 siRNA was eliciting an anti-HSV-1 response in a non-sequence-dependent manner (FIG. 1A).

TABLE 1

Sequence of siRNAs

| Id of siRNAs | 5' sequence 3' (SEQ ID NO:) | Source |
|---|---|---|
| Anti-La#2 | AACTGGATGAAGGCTGGGTAC (10) | Dharmacon |
| Anti-Ro#1 | AATCTGTAAACCAAATGCAGC (11) | Dharmacon |
| Anti-HSV#1 | AACAAGCAGCGCCCCGGCTCC (12) | T7 transcription |
| Anti-HSV#2 | AACAGCAGCTCCTTCATCACC (13) | T7 transcription |
| Anti-SF3A3#1 | AAGGAACGGCTCATGGACGTC (14) | T7 transcription |

Figure 1B:
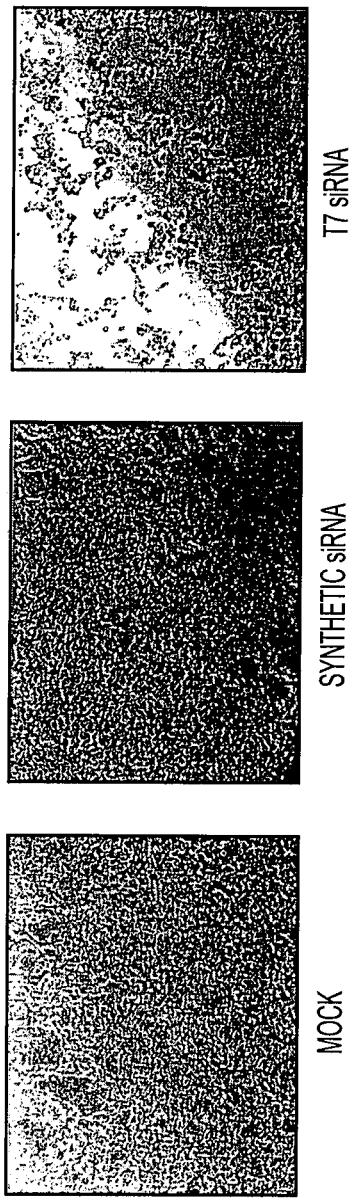
FIG. 1B are photographs showing the cytotoxic effect of T7 transcribed siRNAs. HEK-293 cells were transfected with 20 nM of synthetic or T7 transcribed siRNA and monitored microscopically on day 5 post transfection.

To further investigate the nature of the T7 siRNA-mediated inhibition of HSV-1 infection, HEK-293 cells were transfected with the chemically synthesized or T7-transcribed siRNAs and monitored for cell growth. The T7 siRNA-transfected cells underwent cell death after 5 days, indicative of possible activation of the interferon response pathway in response to the T7 transcripts (FIG. 1B). It was also found that the anti-HSV-1 effect was transferable with the medium of T7 siRNA-transfected cells, evidence of secreted protein(s), which further supports the likelihood of an interferon-mediated response. To verify the presence of an interferon-mediated response, the medium of T7 siRNA-transfected cells was assayed for interferon α and β using an enzyme-linked immunosorbent assay (ELISA). Substantial amounts of both interferons were induced by transfection of 10 nM of the T7 siRNAs (Table 2).

TABLE 2

Induction of interferon by the T7 siRNAs

| SiRNA (10 nM) | Amount of Interferon α (pg/ml) | Amount of Interferon β (pg/ml) |
|---|---|---|
| Mock | 0.2 ± 0.3 | 3 ± 2 |
| Synthetic siRNA | 2 ± 0.5 | 5 ± 5 |
| T7 siRNA 1 (anti-La #2) | 300 ± 85 | 4,000 ± 300 |
| T7 siRNA 2 (anti-Ro #1) | 250 ± 35 | 3,500 ± 300 |

Figure 2A:
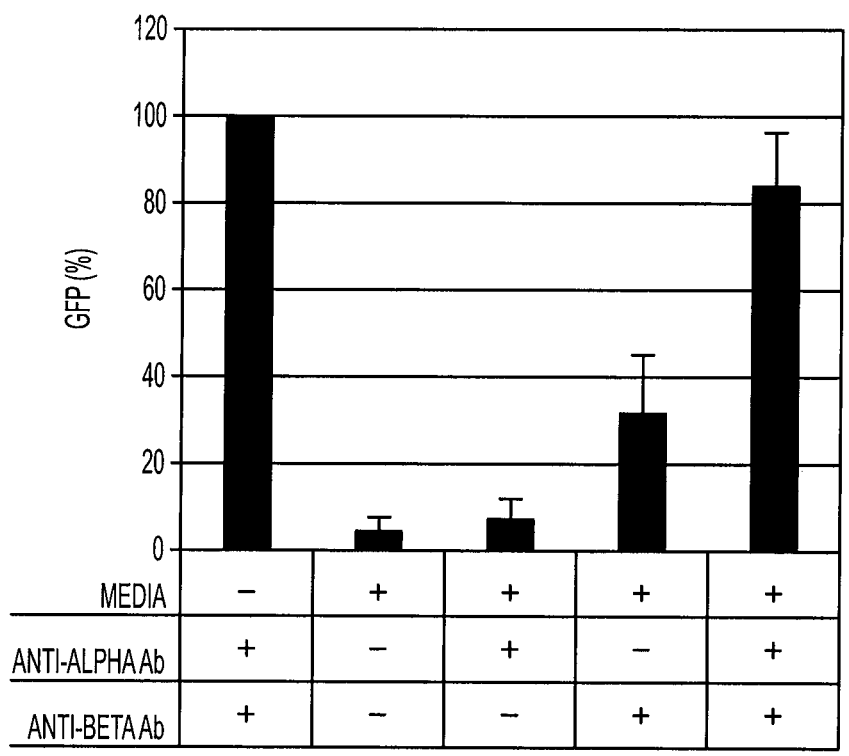
FIGS. 2A-2D show interferon induction by transcribed siRNAs.

To confirm that the anti-HSV-1 effect was mediated by the interferons, HSV-1 infection was tested using medium from T7 siRNA-transfected cells previously treated with neutralizing antibodies (FIG. 2a). A combination of antibodies to interferon α and β was required to neutralize the inhibition, suggesting that both interferons are mediating the antiviral response. In this embodiment, inhibition of HSV-1 infection took place preferably when cells were pretreated with the T7 siRNAs, or in another preferred embodiment when medium from the T7 siRNA-treated cells was added to a fresh cell culture before HSV-1 challenge. These results are consistent with the known mechanisms of interferon inhibition of HSV-1 and the anti-interferon mechanism of this virus, which shuts down the host response during infection (Samuel, C. E., 2001). In this embodiment, the interferons were induced before infection, presumably triggering the expression of antiviral genes (Samuel, C. E., 2001).

Figure 2B:
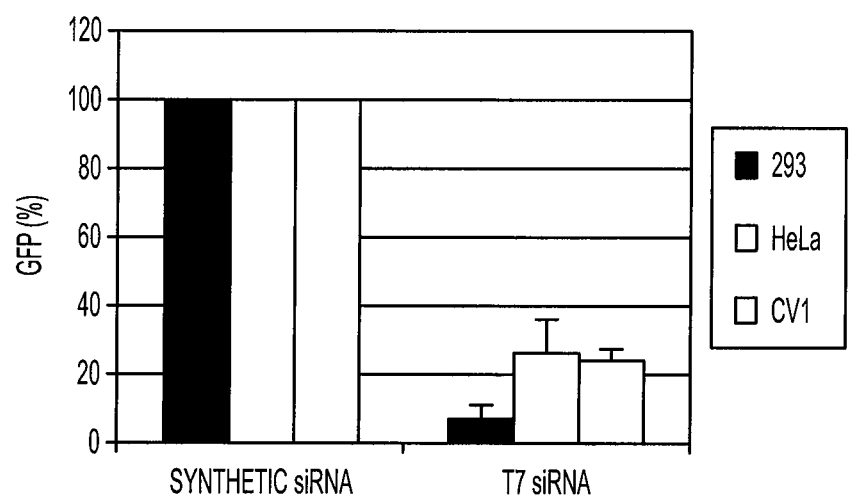

Because the initial experiments in the above embodiment were done with HEK-293 cells, and at least one report shows that HEK-293 cells lack an antiviral interferon response (Stojdl, D. F., et al., 2000), other cell lines were tested for their T7 siRNA-mediated interferon response. For example, both HeLa cells and African Green Monkey kidney fibroblasts (CV1) were transfected with either chemically synthesized or T7 transcribed-siRNAs (FIG. 2b). In each case the T7 transcripts elicited a non-sequence-dependent inhibition of HSV-1, whereas the chemically synthesized siRNAs did not. Next, a different batch of HeLa cells obtained from the ATCC were tested and a similar level of interferon induction was found. In other embodiments, T7 siRNA-mediated interferon levels were measured in media from K562, CEM and Jurkat cells transfected with T7 siRNAs, and again interferon induction was observed in each of these media.

Figure 2C:
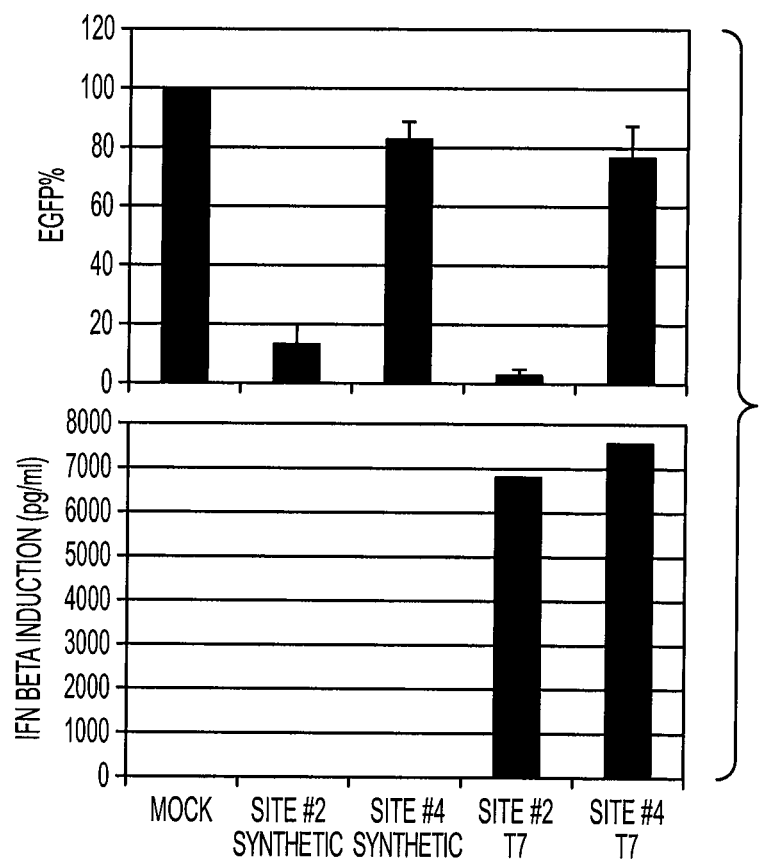
Figure 2D:
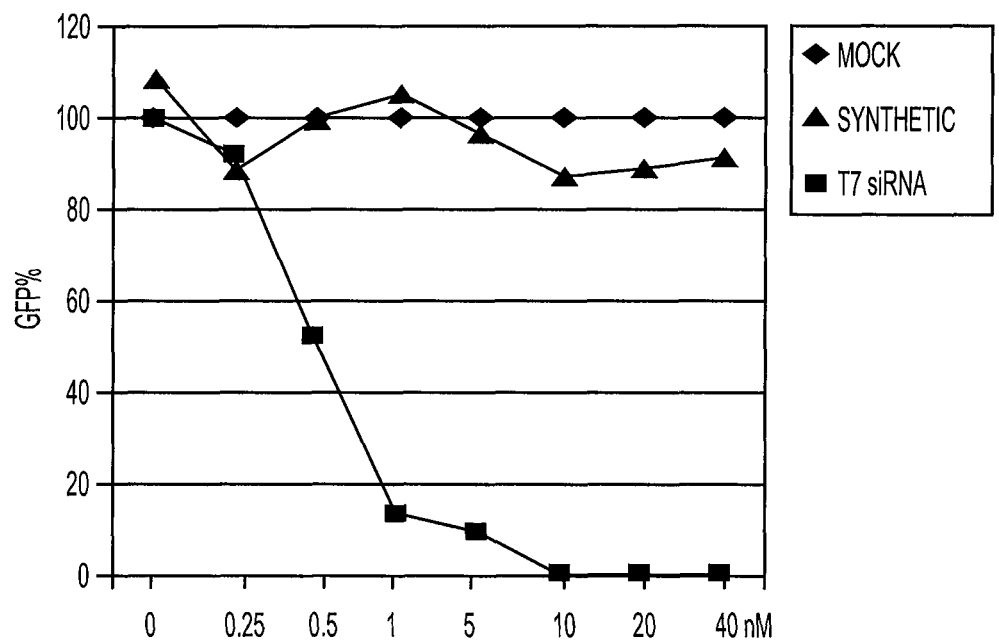

Further, siRNAs targeting EGFP itself were chemically synthesized or transcribed in vitro by T7 RNA polymerase (FIG. 2C). Two different sites in EGFP were chosen, one that is highly susceptible to siRNA knockdown, and one that is not (Kim, D. H. and Rossi, J. J., 2003). When EGFP expression was monitored, the T7 siRNAs showed more potent RNAi than the synthetic siRNAs (FIG. 2C, top, col. 2 versus 4, 3 versus 5). Each of the T7 siRNAs also showed potent interferon induction, indicating that the potency of the knockdown and the interferon induction are two independent phenomena. Unlike the T7 siRNAs, chemically synthesized siRNAs did not induce interferon (FIG. 2C, bottom, col. 2, 3). In addition to the EGFP analyses, the anti-HSV-1 activities of the chemically synthesized versus the T7-transcribed siRNAs were assayed. Up to 200 nM synthetic siRNAs did not inhibit HSV-1, whereas T7-transcribed RNAs completely inhibited HSV-1 at approximately 5 nM (FIG. 2D).

Figure 3A:
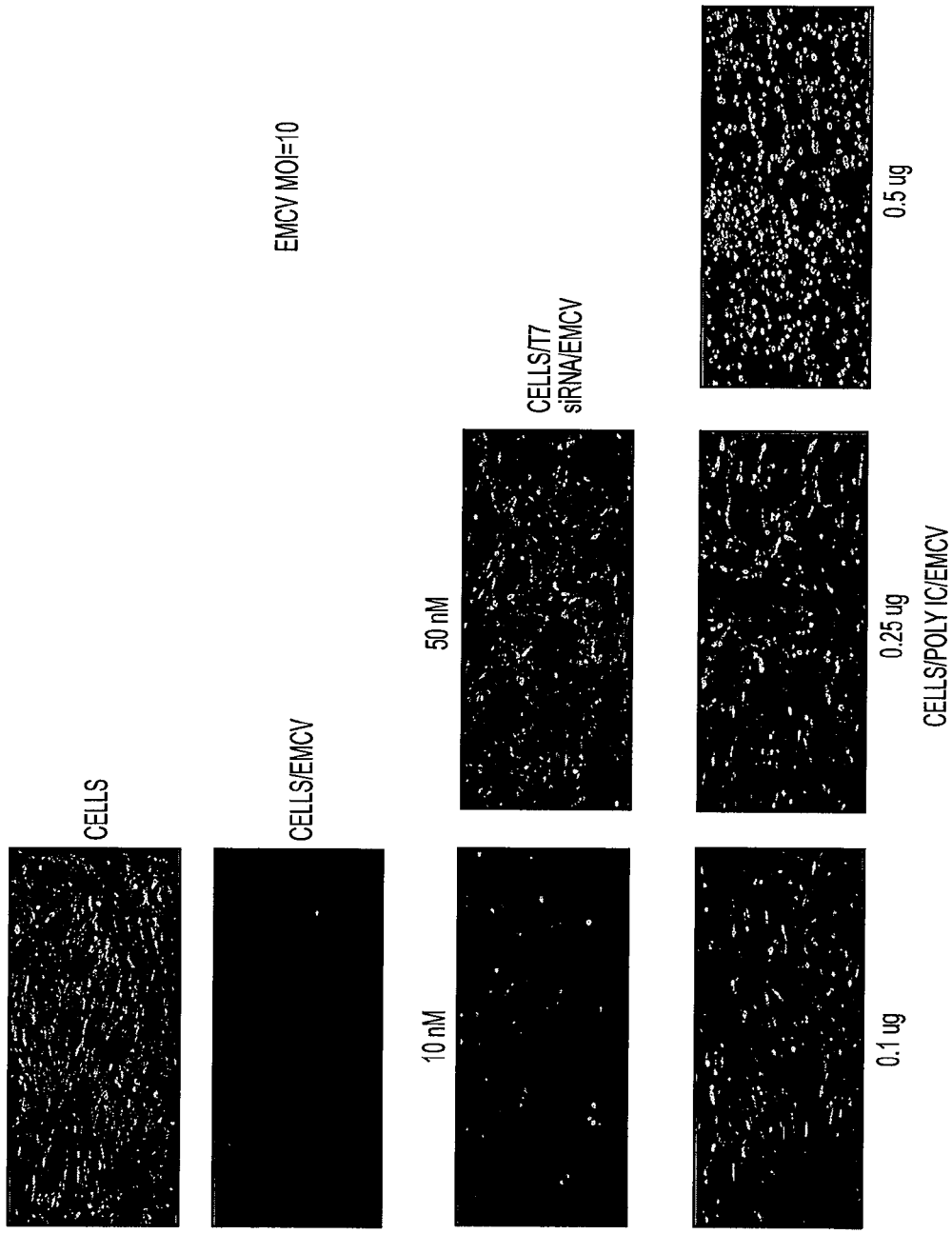
FIG. 3A are photographs showing the anti-EMCV activities of T7 transcribed siRNAs, produced in accordance with the present invention, compared with the anti-EMCV activities of Poly IC. Top panel, cells; Second panel from top, Cells infected with EMCV; Third panel from top, T7 siRNA transfected cells infected with EMCV (triphosphate containing anti-EMCV T7 siRNAs stimulate interferon, thus, protecting cells from EMCV infection); Bottom panel, Poly IC transfected cells infected with EMCV (poly IC is toxic and cells are expressing EGFP, so toxicity results in cell death and loss of EGFP signal.)
Figure 3B:
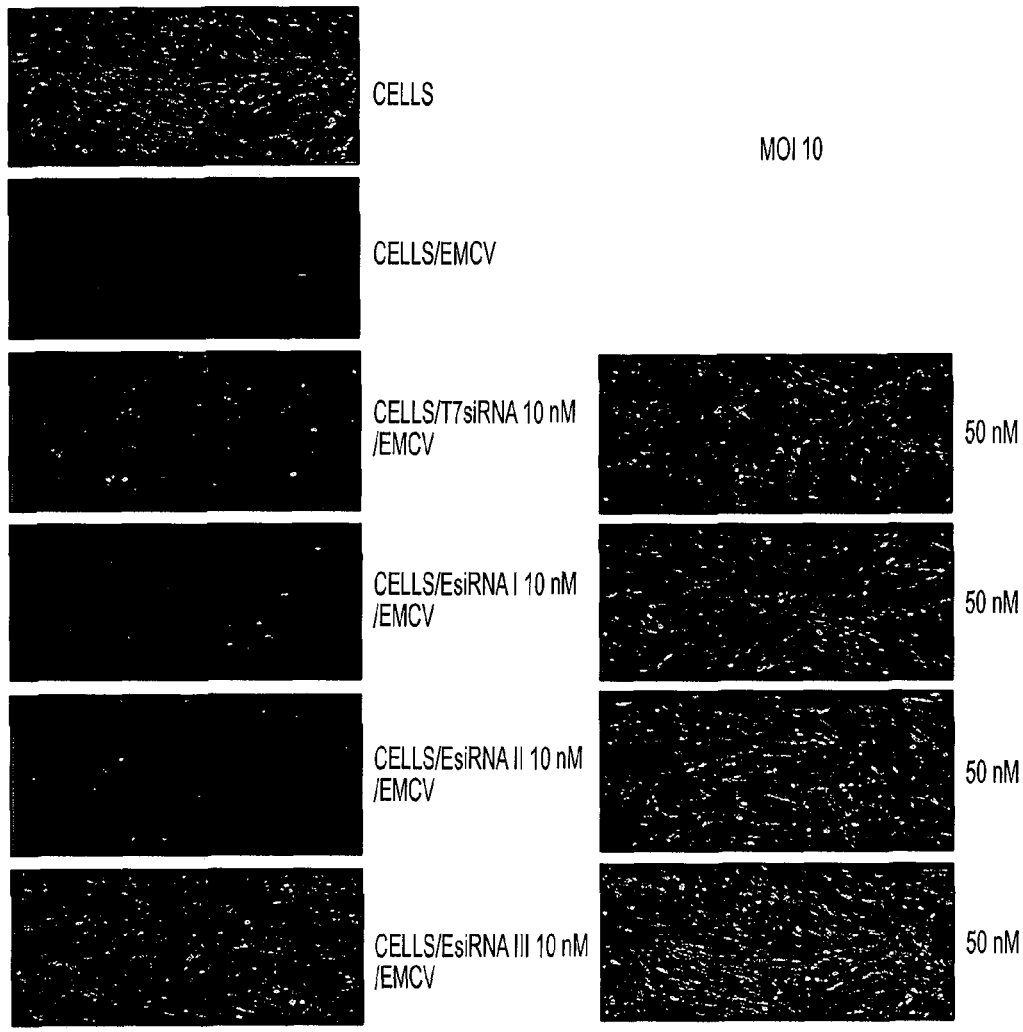
FIG. 3B are photographs showing anti-EMCV activities of T7 transcribed siRNAs, produced in accordance with the present invention, compared with the anti-EMCV activities of various endoribonuclease prepared siRNAs (EsiRNA I, II, and III).
Figure 3C:
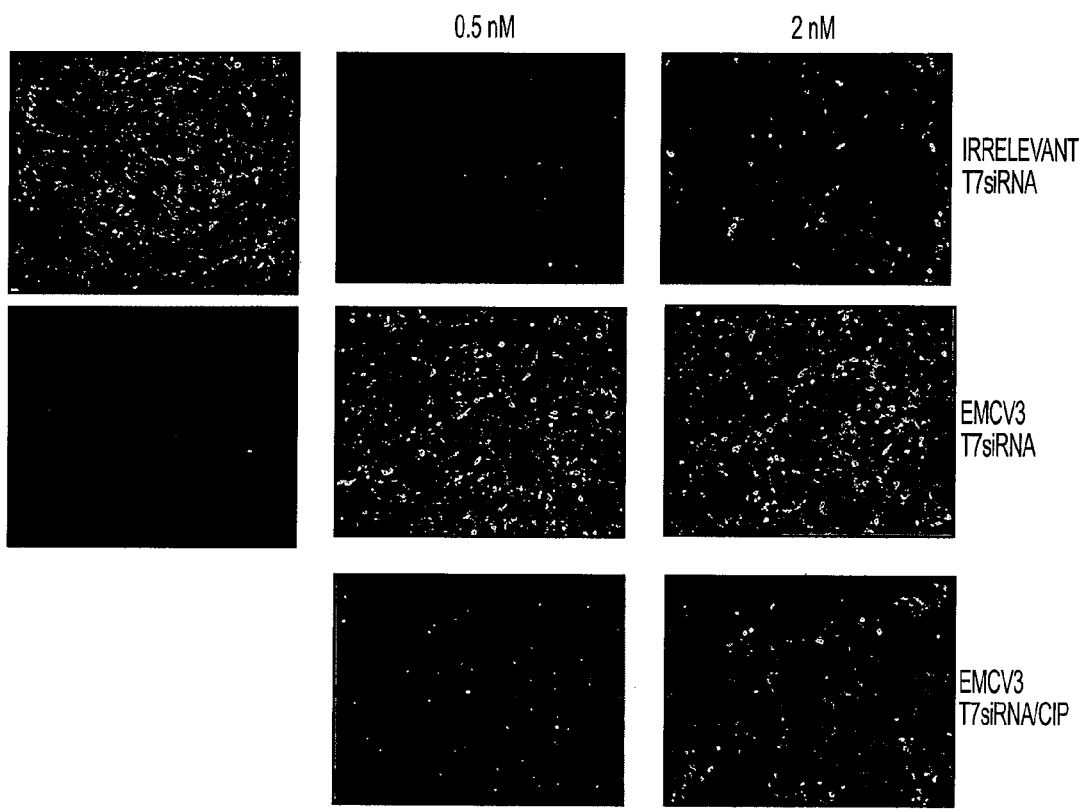
FIG. 3C are photographs showing anti-EMCV3 activities of T7 transcribed siRNAs, produced in accordance with the present invention. Top panel, irrelevant T7 siRNA; Middle panel, EMCV3 T7 siRNA; Bottom panel, EMCV3 T7 siRNA in the presence of CIP.

To test for interferon induction and antiviral activity of an RNAi molecule, additional tests were preformed in connection with other embodiments using RNAi molecules and other viruses, for example, encephalomyocarditis virus (EMCV). An anti-EMCV siRNA having a 5'-triphosphate, which was produced by a bacteriophage T7 RNA polymerase, was created and introduced into cells. Polyinosinic-polycylidylic acid (Poly IC) was also introduced into cells. EMCV was added to the cultured cells at a multiplicity of infection (MOI) of 10 and the results are shown in FIG. 3A. Triphosphate containing anti-EMCV T7 siRNAs stimulate interferon, thus protecting cells from EMCV infection (FIG. 3A, third panel from top). In contrast, poly IC is toxic, as seen in FIG. 3A, bottom panel. Cells are expressing EGFP, so toxicity results in cell death and loss of EGFP signal. Additional experimental results obtained under various conditions also are shown in FIGS. 3B and 3C.

In other embodiments, (HEK) 293, HeLa and 3T3 cells were exposed to T7 siRNAs, made in accordance with the present invention. (HEK) 293, HeLa and 3T3 cells were also exposed to Poly IC. Cell type specific Poly IC and T7 triphosphate siRNA interferon responses in the different cells under various conditions are shown in Table 3 below.

TABLE 3

Cell type specific Poly IC and T7 triphosphate siRNA responses

| | Transfected RNA | Amount | Toxicity on day 2 | Interferon beta (pg/ml) |
|---|---|---|---|---|
| 293 | Mock | | − | 0 |
| | T7 siRNA | 10 nM | − | 300 ± 50 |
| | Poly IC | 50 ng | − | 10 ± 10 |
| | Poly IC | 100 ng | + | 10 ± 5 |
| | T7 siRNA + Poly IC | 10 nM + 50 ng | − | 20 ± 5 |
| HeLa | Mock | | − | 0 |
| | T7 siRNA | 10 nM | − | 250 ± 100 |
| | Poly IC | 50 ng | − | 0 |
| | Poly IC | 100 ng | + | 20 ± 10 |
| | T7 siRNA + Poly IC | 10 nM + 50 ng | − | 0 |
| 3T3 | Mock | | − | 0 |
| | T7 siRNA | 10 nM | − | 300 ± 75 |
| | Poly IC | 250 ng | − | 250 ± 50 |
| | Poly IC | 500 ng | + | 200 ± 50 |
| | T7 siRNA + Poly IC | 100 nM + 250 ng | − | 350 ± 75 |

Table 3 shows the advantages of T7 triphosphate siRNAs over Poly IC in the three different cell types. For example, T7 triphosphate siRNAs are less toxic than Poly IC. They also exhibit a more potent induction of interferon $\beta$ and a strong antiviral effect.

In another embodiment, the invention provides a method for inducing an anti-viral response in a cell comprising introducing into a cell, preferably a mammalian cell, an RNAi molecule having a triphosphate, preferably a 5'-triphosphate, wherein the RNAi molecule induces a synergistic effect resulting from an RNAi molecule-mediated RNAi effect together with a 5'-triphosphate-mediated interferon response.

In another embodiment, the invention provides an antiviral reagent comprising an RNAi molecule having a triphosphate, preferably a 5'-triphosphate, wherein the RNAi molecule induces both an RNAi effect and an interferon response.

In a preferred embodiment, the RNAi molecule having a 5'-triphosphate, can be produced in vitro by a bacteriophage T7 RNA polymerase. In other embodiments of the invention, the RNAi molecule having a 5'-triphosphate can be produced by other phage polymerases, including but not limited to, a bacteriophage T3 RNA polymerase and a bacteriophage Sp6 RNA polymerase. In another embodiment, the RNAi molecule having a 5'-triphosphate is chemically synthesized.

In preferred embodiments, the RNAi molecule having a 5'-triphosphate is a siRNA or a shRNA molecule. The RNAi molecule, or other double-stranded RNA molecule, can be those otherwise known in the art.

In the above embodiment, when an RNAi molecule having a 5'-triphosphate, preferably a short dsRNA and more preferably an siRNA, is designed in a sequence specific manner, potent anti-viral effects can be detected as the result of synergistic effects of the 5'-triphosphate mediated innate immune response, i.e., interferon mediated response, of cells and the siRNA mediated RNAi effect (FIG. 4). Since this anti-viral effect is much more than a simple additive effect of an interferon response and siRNA mediated RNAi, the RNAi molecule can be a powerful anti-viral reagent.

Figure 5A:
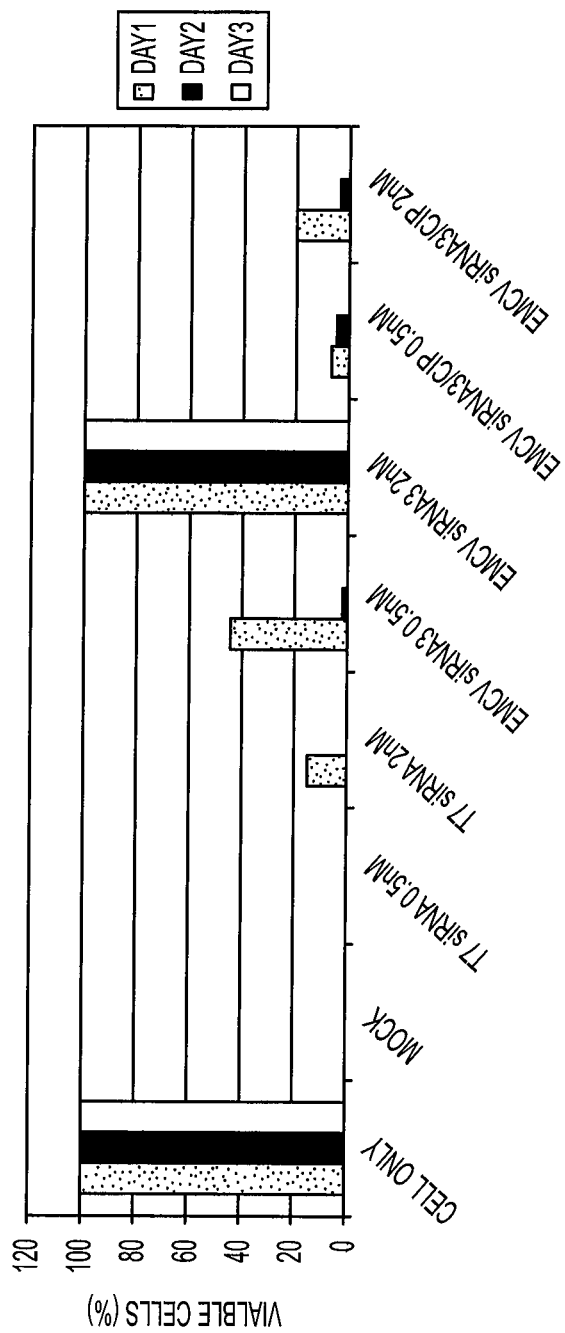
FIG. 5A is a graph showing the synergistic effect of siRNAs and triphosphates in protecting cells from cytopathic effects of EMCV infection at a MOI of 3. T7 siRNA is an siRNA molecule that has been transcribed by T7 polymerase and that is non-target specific. EMCV siRNA3 is an siRNA molecule that has been transcribed by T7 polymerase and is target specific to the sequence shown in FIG. 6. EMCV siRNA3/CIP is EMCV siRNA3 that has been treated with calf intestine phophatase (CIP). The "cell only" are cells that have not been infected with EMCV.
Figure 5B:
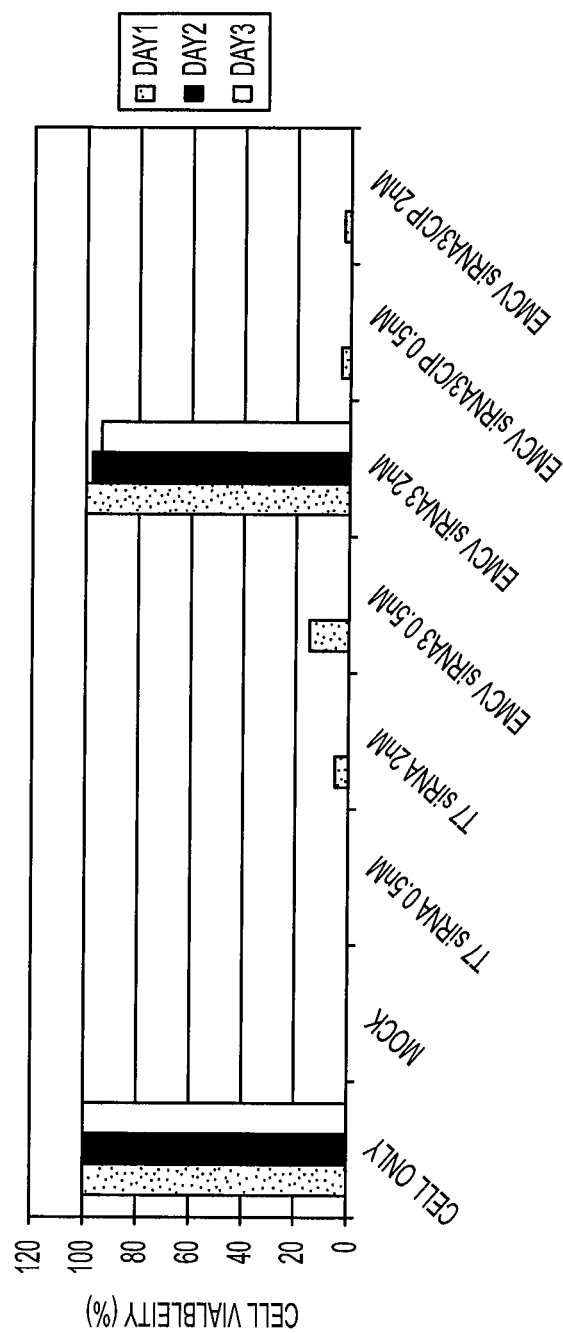
FIG. 5B is a graph showing the synergistic effect of siRNAs and triphosphates in protecting cells from cytopathic effects of EMCV infection at a MOI of 10. T7 siRNA is an siRNA molecule that has been transcribed by T7 polymerase and that is non-target specific. EMCV siRNA3 is an siRNA molecule that has been transcribed by T7 polymerase and is target specific to the sequence shown in FIG. 6. EMCV siRNA3/CIP is EMCV siRNA3 that has been treated with calf intestine phophatase (CIP). The "cell only" are cells that have not been infected with EMCV.

In a preferred embodiment, FIG. 5A shows the synergistic effect of siRNAs and triphosphates in protecting cells from the cytopathic effects of EMCV infection at a MOI of 3. In another embodiment, FIG. 5B shows the synergistic effect of siRNAs and triphosphates in protecting cells from the cytopathic effects of EMCV infection at a MOI of 10.

Another embodiment of the present invention provides a method for inducing an interferon response in a cell, comprising introducing into the cell, preferably a mammalian cell, a single stranded RNA (ssRNA) having a triphosphate, preferably a 5'-triphosphate, wherein the presence of the 5'-triphosphate induces the interferon response. In a preferred embodiment, the ssRNA having a 5'-triphosphate induces one or more of interferon α and β.

In a preferred embodiment, the ssRNA having a 5'-triphosphate is produced in vitro by a bacteriophage RNA polymerase. More preferably the ssRNA having a 5'-triphosphate is produced in vitro by a bacteriophage T7 RNA polymerase. In other embodiments, the ssRNA having a 5'-triphosphate may be produced by other phage polymerases, including but not limited to, a bacteriophage T3 RNA polymerase and a bacteriophage Sp6 RNA polymerase.

In another embodiment, the ssRNA having a triphosphate can be chemically synthesized.

The preferred lengths of short ssRNAs having a triphosphate, preferably a 5'-triphosphate, are expected to be roughly the same as for double-stranded RNA molecules. At least one difference is that the effect of length of a ssRNA molecule may vary depending on the cell type. For example, while some cells show an effect similar for dsRNAs, others may not as a result of being mediated by different nuclease activity. In particular, similar effects can occur in both ssRNA and dsRNA in certain cell lines, such as HEK 293 cells, while in other cell lines lesser of an effect may be observed with ssRNA on account of ssRNA being less stable than dsRNA.

In another embodiment, an antiviral response can be induced by introducing into a cell an ssRNA having a triphosphate, preferably a 5'-triphosphate, wherein the presence of the 5'-triphosphate induces an interferon response as well as an anti-viral response. In another embodiment, the ssRNA is introduced into a cell prior to viral infection, and thereby inhibiting viral infection. Viruses include, for example, herpes simplex virus 1 (HSV-1), EMCV or Influenza virus A, as well as other viruses.

Figure 8A:
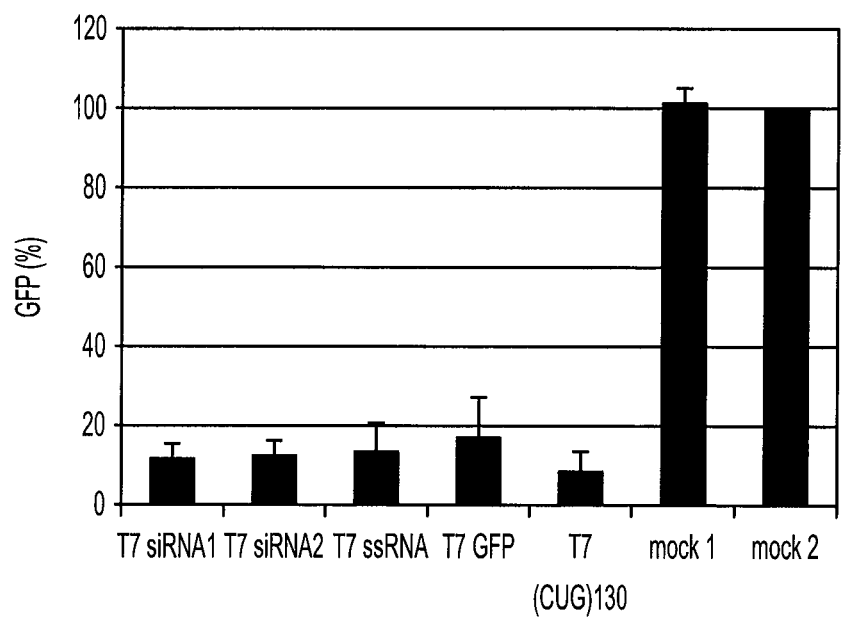
FIGS. 8A-8C show induction of interferon by in vitro transcribed ssRNAs.
Figure 8B:
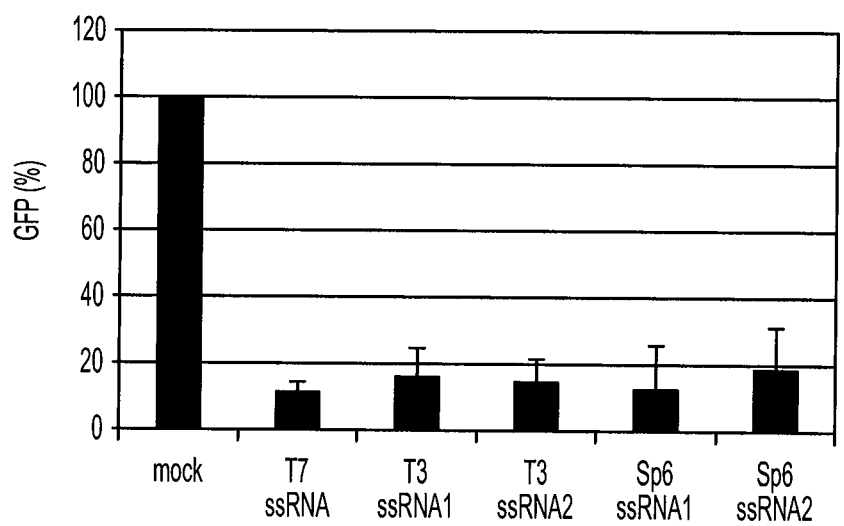

To confirm the role of the triphosphate, T7 RNA polymerase-transcribed ssRNAs were tested as well (FIG. 8A). No HSV-1 inhibition was observed when cells were transfected with the RNase A-treated ssRNAs (FIG. 8A, mock 1) or T7 ssRNA in the absence of a transfection reagent (FIG. 8A, mock 2), but anti-HSV-1 activity was observed when cells were transfected with a non-RNAse-treated-ssRNA in the presence of cationic lipid. Additional experiments were carried out in other embodiments using ssRNAs transcribed by the bacteriophage T3 and Sp6 RNA polymerases (FIG. 8B). Each of these transcripts also elicited anti-HSV-1 activity.

Interferon assays from these experiments indicate that the ssRNAs are also potent inducers of interferons (Table 4).

TABLE 4

Induction of interferon mediated by various in vitro transcribed RNAs.

| RNAs | | Amount of Interferon-α (pg/ml) | Amount of Interferon-β (pg/ml) |
|---|---|---|---|
| T7 siRNA[1] | 10 nM | 300 ± 85 | 4,000 ± 300 |
| | 40 nM | 650 ± 100 | 9,500 + 500 |
| T7 single stranded RNA[2] | 10 nM | 580 ± 120 | 8,000 ± 250 |
| | 40 nM | 1050 ± 280 | 10,000 ± 500 |
| T3 single stranded RNA[3] | 10 nM | 620 ± 180 | 7,000 ± 500 |
| | 40 nM | 1000 ± 240 | 10,000 ± 1000 |
| Sp6 single stranded RNA[4] | 10 nM | 600 ± 50 | 7,000 ± 500 |
| | 40 nM | 800 ± 80 | 8,000 ± 300 |

[1]Anti-La #2 siRNA.
[2]The sense RNA of HSV #1.
[3]The T3 transcript from the BamHI digested pBluescript DNA template.
[4]The Sp6 transcript from the SalI digested pGEM9Df(−) DNA template.

Figure 8C:
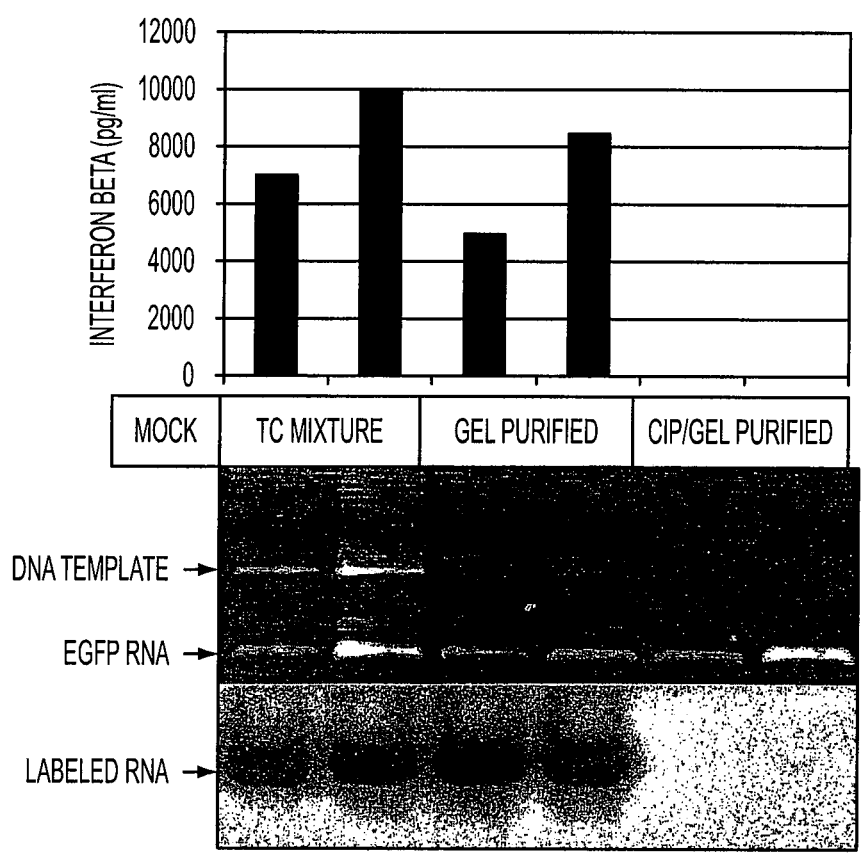

The ssRNAs were transcribed in the presence of [γ-$^{32}$P] GTP and analyzed by gel electrophoresis confirming their single stranded nature (FIG. 8C, middle and bottom). These ssRNAs all induce interferon, but this capacity is lost when these RNAs are treated with calf intestine phosphatase (CIP) (FIG. 8C).

In another embodiment, the present invention provides a method for inhibiting the interferon inducing activity of a RNAi molecule having a 5'-triphosphate comprising removing, preferably by cleaving, the 5'-triphosphate and/or the initiating 5' nucleotides, from the RNAi molecule, wherein removal of the 5'-triphosphate and/or nucleotides reduces the interferon inducing activity of the RNAi molecule while still maintaining partial or full efficacy.

In a preferred embodiment, means are incorporated at the 3' terminus of the RNAi molecule to prevent base pairing with the initiating 5' nucleotides, preferably 5' guanines, of the molecule. In one embodiment, at least two bases, preferably one or more adenosines, are incorporated at the 3' terminus of the RNAi molecule to prevent base pairing with one or more initiating 5' guanines of the RNAi molecule prior to cleaving the 5'-triphosphate and/or nucleotides from the RNAi molecule. Incorporation of the bases thereby allows the cleavage means, preferably a ribonuclease and/or phosphatase, to remove the initiating 5'-triphosphates and/or nucleotides of the transcripts.

In another preferred embodiment, the invention provides a method for inhibiting interferon inducing activity of a ssRNA having a 5'-triphosphate comprising removing, preferably by cleaving, the 5'-triphosphate and/or initiating 5' nucleotides from the ssRNA, wherein removal of the 5'-triphosphate and/or nucleotides reduces the interferon inducing activity of the ssRNA.

The cleavage step is performed preferably by a nuclease, more preferably a ribonuclease, preferably T1 ribonuclease, or by a phosphatase, preferably calf intestine phosphatase (CIP). However, it is understood that other means and enzymes can be used to effect the cleavage.

In a preferred embodiment, the cleavage step is performed by both a ribonuclease and a phosphatase, preferably T1 ribonuclease and calf intestine phosphatase (CIP).

To determine the active interferon-inducing agent in the RNAi molecules, a series of experiments were carried out focusing on the initiating G residues. Because T7 RNA polymerase initiates transcription with 5'-pGGG, a determination was made as to whether the GGG associated with the 5' end of the transcript was the inducing agent by chemically synthesizing the anti-EGFP #2 siRNA (FIG. 7A, EGFP #2 synthetic 1) with a 5'-OH-GGG, and testing this siRNA for interferon induction. No interferon induction in HEK-293 cells was elicited by this siRNA.

Figure 7B:
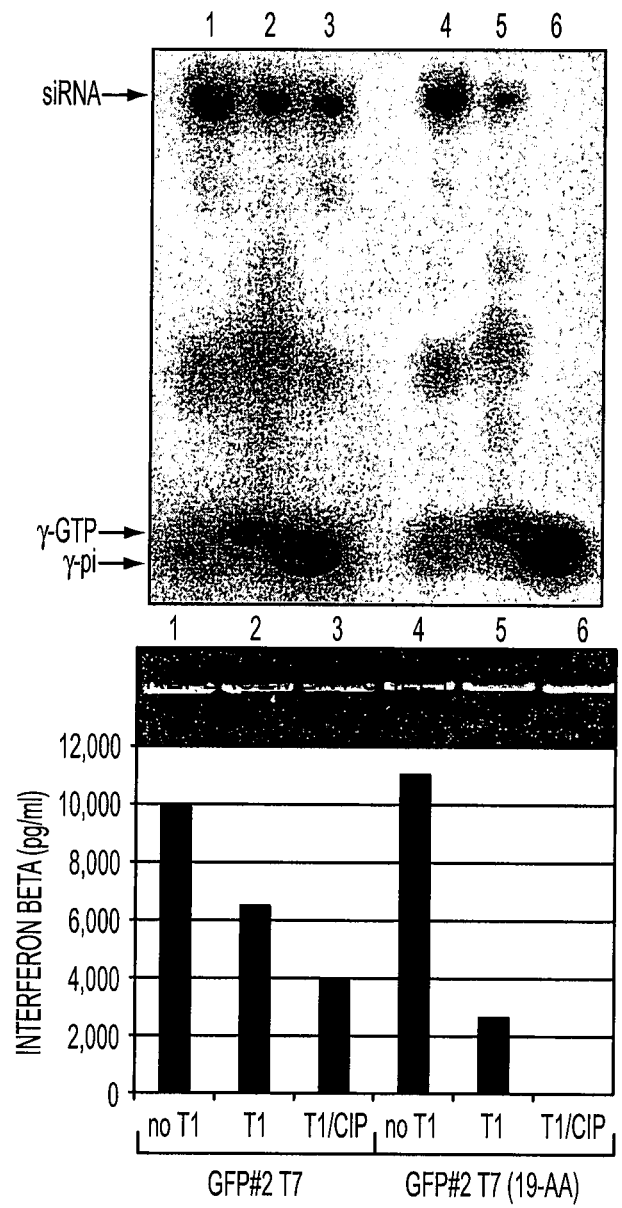

The other major difference between the synthetic and in vitro T7-transcribed siRNAs is the 5' triphosphate. The anti-EGFP #2 siRNA was transcribed by T7 RNA polymerase in the presence of [$\gamma$-$^{32}$P]GTP to label the $\gamma$-phosphate. The initiating pGGG should be cleaved from the transcript by the single strand-specific ribonuclease T1 (Wang, L., et al., 1976) if the Gs are within a single-stranded region of the siRNA. When the anti-EGFP #2 siRNA was treated with RNase T1, there was a modest reduction in interferon induction compared with the untreated siRNA (FIG. 7B, bottom, col. 2). When the RNA was sequentially created with ribonuclease T1 and calf intestine phosphatase (CIP), the interferon induction was further reduced (FIG. 7B, col. 3). For each of these samples, removal of the labeled 5'$\gamma$-phosphate was monitored using native gel electrophoresis (FIG. 7B, top). From these analyses it was concluded that the residual amount of siRNA containing 5'$\gamma$-triphosphate was proportional to the extent of interferon induction.

Given that the ribonuclease T1 treatment of the anti-EGFP #2 siRNA did not completely remove the 5'-pGGG, it was reasoned that perhaps it or the adjacent Gs were involved in wobble base pairing with the 3' terminal Us of the transcript, making this a poor substrate for the single strand-specific ribonuclease and CIP. To test this possibility, a version of the EGFP #2 siRNA that contained 19 bases complementary to EGFP followed by AA at the 3' end (FIG. 7A, EGFP #2 T7 (19-AA) was transcribed. When this siRNA was treated with T1 and tested in cell culture for interferon induction, there was a reduction relative to the pGGG-containing control (FIG. 7B, col. 5). When this RNA was further treated with CIP, the 5' triphosphate was completely removed along with complete loss of interferon induction (FIG. 7B, col. 6) even at a concentration of 100 nM. Combining these results, it was concluded that the interferon induction observed with the in vitro transcribed siRNAs is linked to the presence of a 5' triphosphate.

Figure 7C:
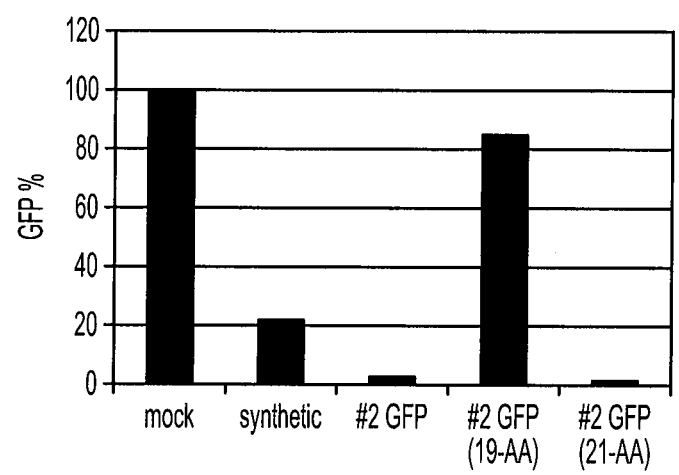

The EGFP #2 T7 (19-AA) siRNA was also tested for EGFP knockdown activity, but it showed little potency (FIG. 7C, col. 4). It was reasoned that because this siRNA now contained a total of only 19 bases complementary to EGFP, it was not as potent as an siRNA with 21 complementary bases. To test this, an siRNA with 21 bases complementary to the same EGFP target and still maintaining the two adenosines at the 3' terminus was created (FIG. 7A, EGFP #2 T7 (21-AA)). This particular siRNA elicited a potent EGFP knockdown (FIG. 7C, col. 5) in the complete absence of an interferon response. Thus, by preventing the formation of base pairs with the initiating Gs, a combination of T1 ribonuclease and CIP treatment completely eliminated the interferon response, while maintaining active RNAi function for these siRNAs.

Moreover, the fact that transcripts containing triphosphates are such potent inducers of interferon makes it of great interest to understand which, if any, of the interferon-linked receptors respond to the triphosphate-containing siRNAs. The triphosphate at the 5'-end of the uncapped negative (genomic) strands of RNA viruses like influenza virus (Honda, et al. 1998) may correspond to the biological substrate targeted by the interferon response seen with T7 ssRNA. To this extent, it is important to understand the biological role that triphosphate induction of interferon plays in normal cellular viral defense mechanisms.

Preferred embodiments of the invention provide an siRNA synthesized from the T7 RNA polymerase system, which can trigger a potent induction of interferon $\alpha$ and $\beta$ in a variety of cell lines. In addition, very potent induction of interferon $\alpha$ and $\beta$ by short single-stranded RNAs (ssRNAs) transcribed with T3, T7 and Sp6 RNA polymerases was also found. Analyses of the potential mediators of this response revealed that the initiating 5' triphosphate is required for interferon induction.

In another embodiment, the present invention provides for short dsRNAs having triphosphates, preferably 5' triphosphates, which are potent enhancers of interferons as well as potential anti-viral reagents. The present invention also provides for the use of short dsRNAs or RNAi molecules, e.g., siRNA or shRNA, transcribed in vitro, and not processed to remove the initiating 5'-triphosphate, which exhibit potent interferon stimulation both in cell culture and in mice. This interferon stimulation may inhibit viral infection if the treatment is provided prior to viral infection, or in some instances, when it is provided after viral infection. Viral infection otherwise is treatable with the present invention.

The present invention answers the question of how the triphosphate-containing siRNAs and ssRNAs induce interferon. For example, when HEK-293 cells were transfected with up to 20 μg total cellular RNA, no interferon induction was observed. In contrast, as little as 1 nM of the in vitro transcribed siRNA initiates the interferon response (FIG. 2D). The antiviral activities of interferons are well studied (Samuel, C. E., 2001), but the present invention is believed to be first to show that the presence of a triphosphate on in vitro transcribed-RNAs can potently induce interferon $\alpha$ and $\beta$, and furthermore elicit a strong, non-sequence-specific anti-viral response to viral challenges, such as HSV-1 challenge. In contrast, other reports in which T7-transcribed siRNAs were used as antiviral agents did not incorporate interferon assays in the analyses (Capodici, J., et al., 2002; Kapadia, S. B., et al., 2003), and thus whether any anti-viral effect was due to interferon induction rather than the RNAi effect was not recognized.

Figure 10A:
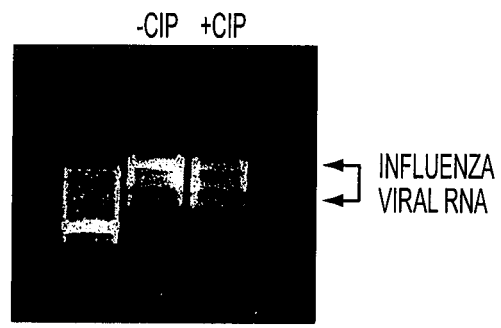
FIGS. 10A-10D show that the 5' triphosphate label of RNA is a novel motif for stimulating the innate immune response.
Figure 10B:
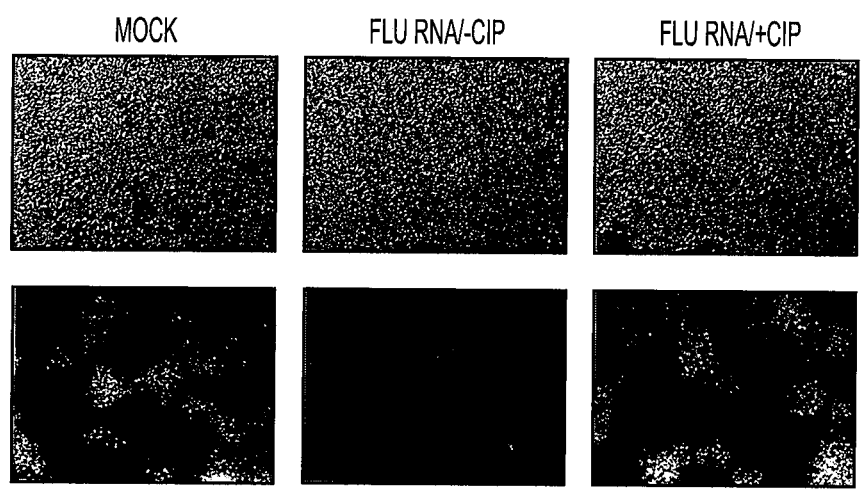

The above shows that short interfering RNAs (siRNAs) prepared by in vitro transcription using T7 RNA polymerase induce potent anti-Herpes Simplex Virus 1 (HSV1) activity that is mediated by the induction of type 1 interferons. The anti-viral activity is dependent on the presence of a 5' triphosphate motif on either strand of the siRNA duplex and the antiviral effects are reversed by simple treatment with calf intestinal phosphatase (CIP). We hypothesized that a host defense system exists which recognizes 5' triphophate-containing viral RNAs. To further characterize the anti-viral properties of the 5' triphosphate motif experiments were performed with genomic RNA derived from the Influenza A virus. Influenza viral RNAs lack 5' modifications since the virus-derived transcriptase is unable to modify the 5' terminus of mRNAs in the cytoplasm (Lamb, R. A. and Choppin, P. A., 1983). Purified influenza viral RNAs were incubated in the presence or absence of CIP prior to transfection into HEK293 cells (FIG. 10A). The cells were sequentially challenged by HSV1 harboring an EGFP reporter gene (Elliott, G. and O'Hare, P., 1999). When cells were pre-transfected with influenza viral RNA, they were protected from HSV1 infection in a manner that was dependent on pre-treatment with CIP (FIG. 10B). The CIP treatment is limited to the removal of the 5' triphosphate and does not affect the integrity of the RNA (FIG. 10A) (Kim, D. H. et al., 2004).

Figure 10C:
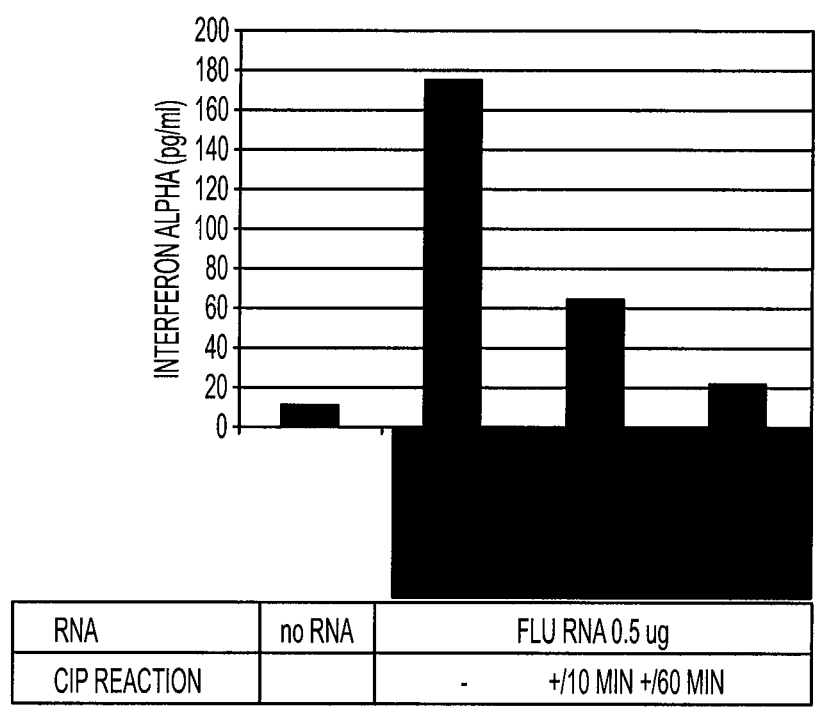
Figure 10D:
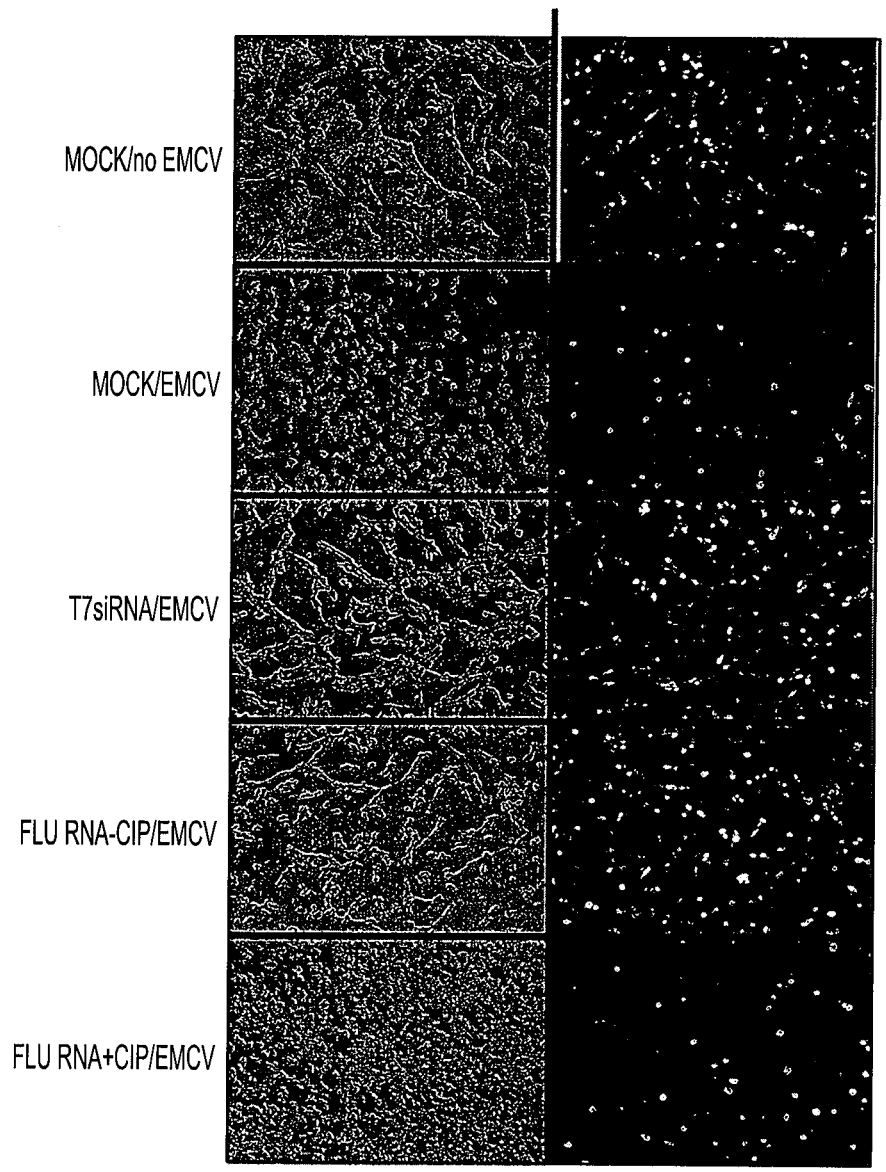

We further investigated if the anti-viral effect is mediated by type 1 interferon induction. The level of interferon α was determined by ELISA (FIG. 10C). Consistent with the results from the anti-HSV response, the induction of interferon α is dependent on CIP treatment, which was shown to be augmented by prolonging the exposure to CIP. To generalize this observation using a different model, the mouse cell line NIH3T3 stably expressing EGFP (Kim, D. H. et al., 2005) was used. When this cell line was infected with Encephalomyocarditis virus (EMCV), the cytotoxic effect of the virus was measured by the loss of EGFP expression (FIG. 10D, the first vs. second row). The cytotoxic effect by EMCV was reduced when the cells were transfected with either T7 RNA or Influenza viral RNA prior to viral challenge (FIG. 10D, third and fourth rows). Clearly the antiviral activity is dependent on the presence of a 5' triphosphate motif on introduced RNA (FIG. 10D, fourth vs. fifth rows) and this property is not limited to human cells.

Figure 11A:
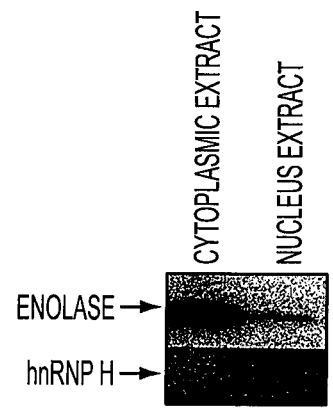
FIGS. 11A-11C shows that the nuclear derived nascent RNAs indicate the dependence of the 5' triphosphate motif for antiviral activity.
Figure 11B:
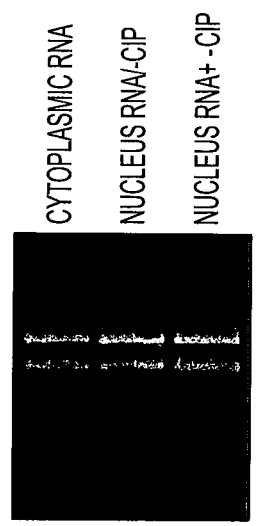
Figure 11C:
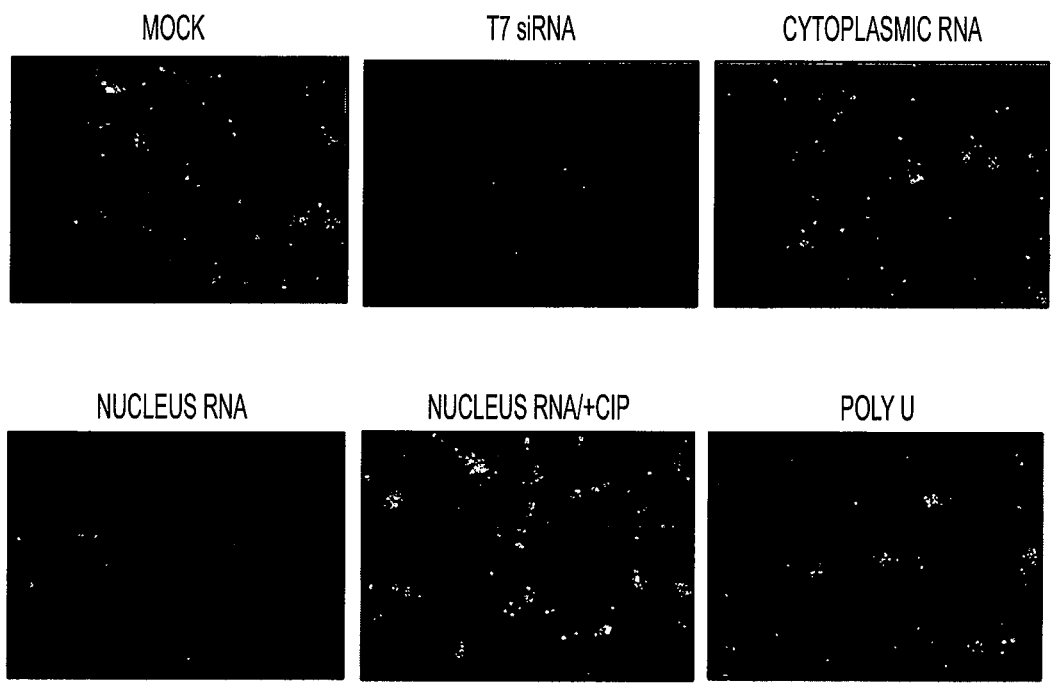

Since a 5' triphosphate group present on any RNA induces an innate immune response, there is the distinct possibility that endogenous cellular RNAs can be potentially immunogenic. Although all nascent transcripts in the nucleus may harbor a 5' triphosphate, it is capped prior to cytoplasmic export (Wei, C. and Moss, B., 1977; Gu, M. and Lima, C. D., 2005). To test whether endogenous cellular RNAs from different compartments can elicit an immune response, cytoplasmic and nuclear extracts of HEK293 cells were prepared. The integrity of the fractionate samples was confirmed by Western blot analyses to detect the nuclear specific hnRNP H (Chou, M. Y., et al., 1999) or cytoplasmic specific enolase (Dolken, G. et al., 1975) (FIG. 11A). The majority of enolase staining was in the cytoplasmic fraction whereas the hnRNP H detection took place only in the nuclear fraction. RNA was purified from each fraction and used in cationic lipid mediated transfections of HEK293 cells (FIG. 1B) which were subsequently challenged with HSV1 (FIG. 11C). RNA derived from the cytoplasmic fraction did not elicit an anti-HSV protective response whereas the nuclear-derived RNAs showed an anti-viral response that could be abrogated by prior treatment with CIP (FIG. 11C). These data indicate that two types of RNAs separated by the nuclear membrane have different immunogenic characteristics mediated by the 5' triphosphate. These results suggest that cells have adopted their antiviral defense strategy based on the biological principal that most if not all cytoplasmic RNAs lack an exposed 5' triphosphate as a consequence of capping. Thus 5'-triphosphate-containing RNAs may be recognized as infectious viral RNAs, thereby activating the innate immune system as a defense mechanism.

Figure 12A:
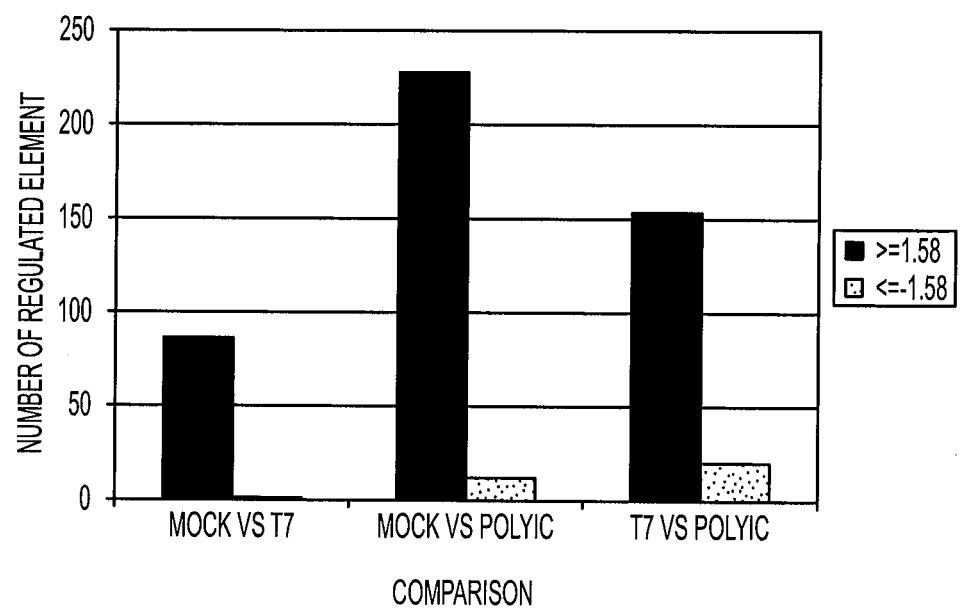
FIGS. 12A-12C show that the T7 RNA and poly IC activate the TLR3 receptor and share similar expression profiles.

A comprehensive profile of gene expression by double-stranded RNA has been previously undertaken (Geis, G. et al., 2001). However, to characterize the signaling pathways elicited by 5'-triphosphate labeled RNA, NIH3T3 cells were transfected with either poly IC or bacteriophage T7-generated RNA (T7 RNA initiates with a tri-phosphate) and their relative gene expression profiles were compared using a murine oligonucleotide microarray. RNA was extracted at three different time points: 4, 8, and 16 hours following transfection with T7 RNA. Unlike the early response induced by Poly IC (Geis, G. et al., 2001), no expression changes were detected until 16 hours post transfection, indicating that the tri-phosphate RNA mediated response takes place more slowly than the Poly IC induced response (data not presented). T7 transcribed RNA resulted in upregulation of the expression of 86 genes among the 16,261 genes on the array when a three-fold threshold was used (FIG. 12A). In a parallel experiment, 229 genes were up-regulated, 12 genes down-regulated in poly IC-transfected cells. Interestingly, all 86 genes upregulated by the T7 transcribed RNA were also upregulated by poly IC (FIGS. 13A-13B), although poly IC activated a large number of additional genes (FIGS. 14A-14D).

To minimize the possibility that poly IC we used in the microarray is contaminated with impure materials such as LPS, additional microarray experiments were performed using purified poly IC or poly IC supplemented with 20 ug/ml polymyxin B, which is a well-characterized LPS inhibitor (Kariko, K., et al., 2004). The identical set of genes was found to be activated under all these conditions (data not presented). Among the genes whose expression was induced by poly IC, several genes related to the apoptosis pathway have been identified as previously reported (FIGS. 14A-14D) (Der, S. D. et al., 1997). When the T7 transcribed RNAs was treated with CIP prior to transfection, the expression profile was identical to that of the non-transfected control cells (data not presented). We confirmed some of the induced gene expression identified in the microarray analyses using quantitative RT-PCR for each representative group of genes. Expression of two genes upregulated in cells transfected with both T7 RNA and Poly IC (Ifi44 and Tgtp) or upregulated when only transfected with Poly IC (Tnf3ip3 and Gadd4alpha) were tested with an internal control (beta-actin) was confirmed in this manner (data not presented).

Figure 12B:
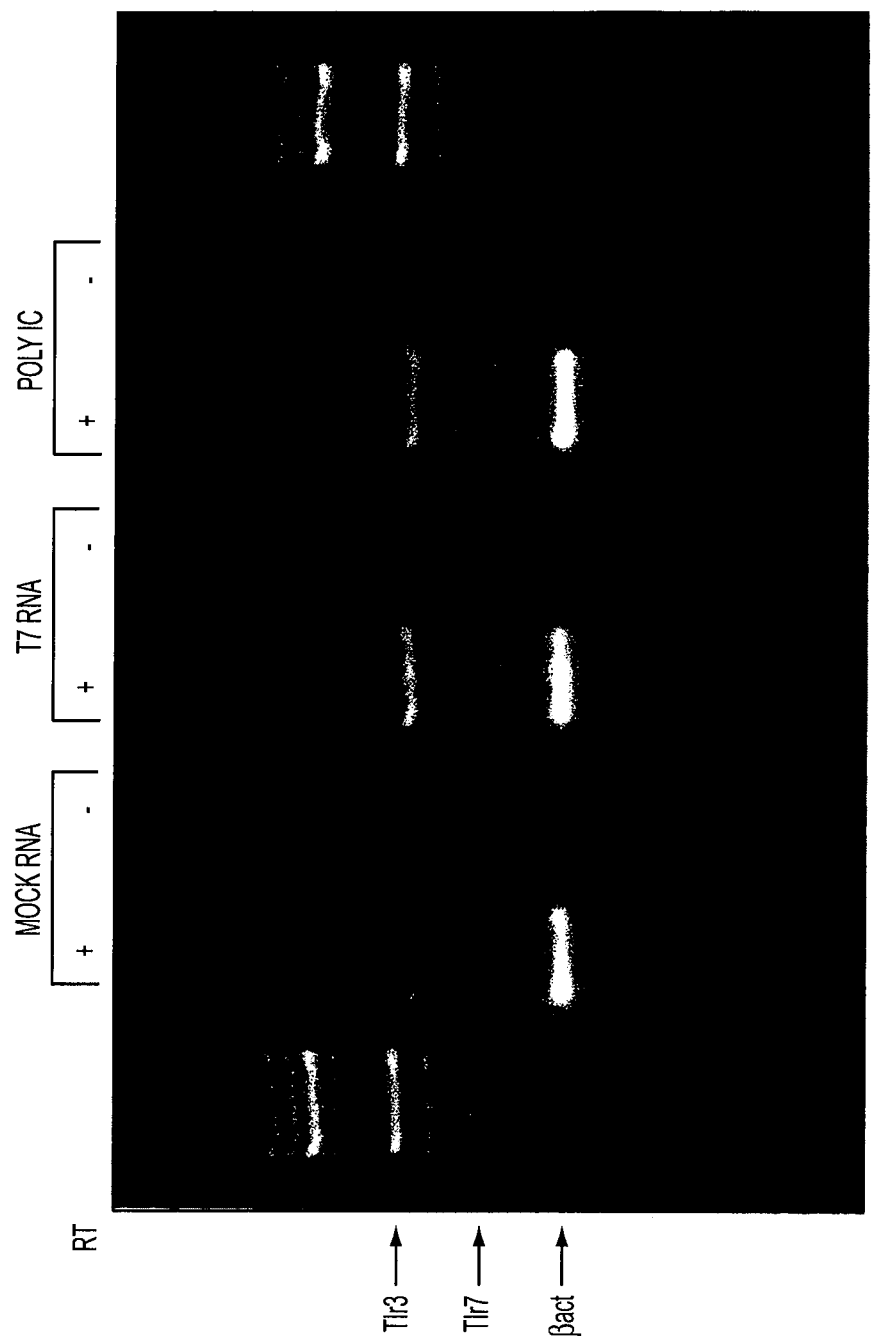
Figure 12C:
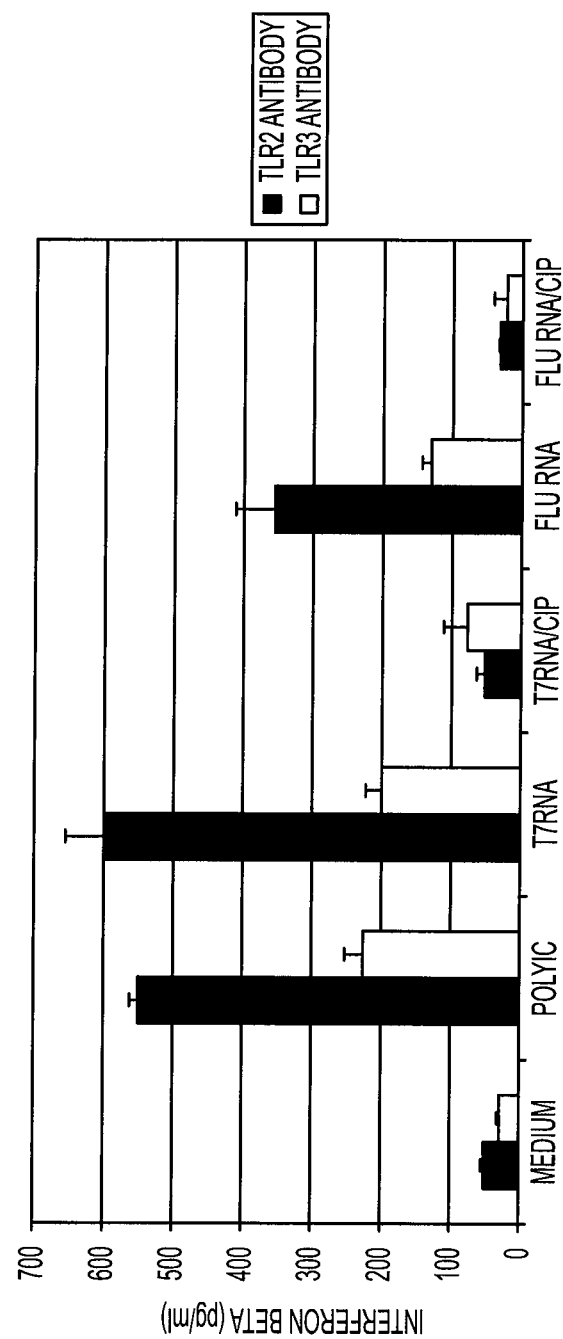

The Toll like receptors respond to pathogens that present certain motifs, termed the pathogen-associated molecular pattern (PAMP), that are displayed on the surface of the invading organisms (Beutler, B., et al., 2004a; Boehme, K. W. and Compton, T., 2004; Beutler, B., 2004b). To define the receptor for the T7 transcribed, tri-phosphate containing RNA, the expression of Toll Like Receptors were compared in microarray data generated from RNA-transfected NIH3T3 cells. The microarray results show that the T7 transcribed RNA induces TLR3 expression (data not presented) which was further confirmed by RT-PCR. TLR3 expression was determined by RT-PCR in poly IC-treated cells, which is known to possess a PAMP for TLR3 (Alexopoulou, L., et al., 2001) (FIG. 12B). Recognition of T7 transcribed RNAs by TLR3 was additionally confirmed by a functional inhibition assay using appropriate antibodies. IFN-β production of poly IC is known to be inhibited by an anti-TLR3 mAb in a human lung fibroblast cell line, MRC-5, which expresses TLR3 on the cell surface (Matsumoto, M. et al., 2002). When T7 transcribed RNA or influenza viral RNA was transfected into these cells, expression levels increased similarly to Poly IC-treated cells (FIG. 12C). Interferon β induction was inhibited when the cells were pre-incubated in the presence of an anti-TLR3 antibody, but not by an anti-TLR2 antibody.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames and S. J. Higgins eds. 1984); *Transcription And Translation* (B. D. Hames and S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish (Danio rerio)*, (4th Ed., Univ. of Oregon Press, Eugene, 2000).

The present invention is described by reference to the following Examples, which are offered by way of illustration and are not intended to limit the invention in any manner. Standard techniques well known in the art or the techniques specifically described below were utilized. Examples 1-5 relate to studies with HSV-1 and ECMV. Examples 6-12 relate to studies with Influenza A virus.

EXAMPLE 1

RNAs

The chemically synthesized RNAs were purchased from Dharmacon. The T7 siRNAs were synthesized using the Silencer siRNA construction kit from Ambion according to the manufacturer's protocol. To transcribe RNA in vitro, T7 primer I (5'-TAATACGACTCACTATA-3' (SEQ ID NO: 15)) was hybridized with T7 primer II, which contains antisense sequence of each transcribed RNA and the tail sequence of 5'-CCCTATAGTGAGTCGTA-3' (SEQ ID NO:16). To make siRNA without interferon induction, the first AA was replaced by TT and included in the T7 primer II. For example, to make GFP #2 T7 (21-AA), two primers were used (5'-TTAAGCTGACCCTGAAGTTCATC-CCCTATAGTGAGTCGTA-3' (SEQ ID NO:17) and 5'-TTGATGAACTTCAGGGTCAGCTTC-CCTATAGTGAGTCGTA-3' (SEQ ID NO: 18)). For the CIP, 20 U of RNAs (NEB) was added to the siRNA after DNase and RNase T1 digestion, and further incubated at 37° C. for 1 h. Final siRNAs were column-purified using conditions recommended for the Silencer siRNA construction kit.

To synthesize the [γ-$^{32}$P]GTP-labeled siRNA, the transcription was done in the presence of 10 mM of cold ATP, CTP and UTP, 2 mM of GTP and [γ-32P]GTP (10 mCi/ml; ICN), and purified using a G50 column (Amersham). For RNAse T1 treatment, the RNA was incubated in the presence of 5 U of RNase T1 in 1× buffer (50 mM Tris-HCl, pH 7.0; 5 mM EDTA; 50 mM NaCl). CIP treatment of EGFP RNA was carried out at 37° C. for 1 h at 1× buffer (100 mM NaCl, 50 mM Tri-HCl, 10 mM MgCl2, 1 mM dithiothreitol (DTT)).

For T3 RNAs, 1 μg of pBluescript DNA template (Stratagen) was digested with either BamHI or EcoRI and used as a template of in vitro transcription using the T3 RNA polymerase (Promega). The Sp6 RNAs were transcribed from the same amount of SalI- or EcoRI-digested pGEM9Df(−) DNA template using the Sp6 RNA polymerase (Promega). All transcription reactions were done under standard reaction conditions and contained 1 μg of linearized DNA template, 2 μl of 100 mM DTT, 2 μl of 10× reaction buffer supplied by each manufacturer, 8 μl of final 2 mM of NTP and 1 μl of each enzyme at 37° C. for 1.5 h. All RNAs were digested with 4U of RNase-free DNAse (Ambion) for 1 h and used in the transfection assay.

EXAMPLE 2

Transfection and RNAi Assay

All transfection assays were done using Lipofectamine 2000 following the manufacturer's protocol (Invitrogen). HEK-293 cells at ninety percent confluency were transfected in 24-well plates with the reporter genes and siRNAs. 250 ng of the pLEGFP-C1 vector (Clontech) and 10 nM of each anti-EGFP siRNA were cotransfected. EGFP expression levels were determined 24 h later from the mean number of EGFP-fluorescent cells determined by fluorescence-activated cell sorting (FACS) analyses. Percentages of EGFP expression were determined relative to nonspecific controls.

For monitoring of cell death, the medium from transfected cells was changed 24 h after transfection. Additional media changes were made after 48 h, and the plates were examined microscopically after another 48 h incubation.

EXAMPLE 3

Anti-HSV-1 Assays

60% confluent HEK-293 cells were transfected in 24-well dishes with siRNA or ssRNA using Lipofectamine 2000 (Invitrogen) according to the manufacturer's protocol. The cells were placed in fresh medium 18 h after transfection. The cells were infected 6 h later with HSV-1 expressing EGFP at an MOI of 1. Cells were subject to FACS analyses 24 h after infection to determine levels of EGFP expression.

EXAMPLE 4

Assays for Interferon α and β

The amount of interferon α and β secreted into the growth medium was determined using interferon ELISA kits (RDI). The medium from Lipofectamine-complexed, RNA-transfected HEK-293 cells was collected 24 h after the initial infection. The medium was serially diluted and assayed for the amount of secreted interferon according to the manufacturer's protocol. Each assay was carried out in triplicate. The antibody neutralization assays were carried out as follows. Neutralizing antibodies for interferon α and β were purchased from RDI. The medium was collected 24 h after transfection with 40 nM of T7 ssRNA. The medium was next diluted 3.3% with the fresh medium and mixed with 100 U/ml of one or both interferon neutralizing antibodies for 1 h. The antibody-treated medium was added to the cell cultures and left for 24 h before HSV-1 challenge.

EXAMPLE 5

Interferon Assay in Mice

Figure 9:
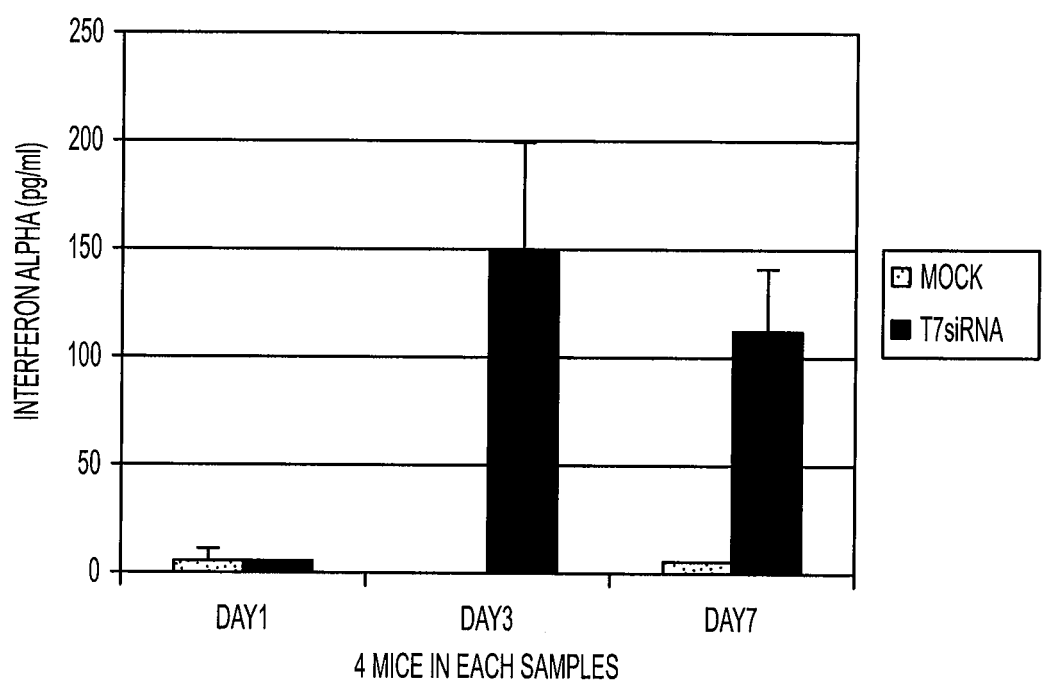
FIG. 9 is a graph showing induction of interferon α in 4 mice samples which were injected with 70 uM triphosphate T7 siRNAs produced in accordance with the present invention. Interferon α induction is shown in mice using mouse ELISA kit at day 1, day 3 and day 7 following injection of T7 siRNA.

An assay for interferon can be performed to detect interferon induction by triphosphate siRNAs, produced in accordance with the present invention, in mice. The effect of T7 siRNA in 4 mice samples was observed by measuring interferon α induction at day 1, day 3 and day 7 following injection of T7 siRNA. (FIG. 9). Assays were performed as follows: (1) Inject mouse with saline (mock) or 70 μM triphosphate siRNAs minus triphosphate or 70 μM triphosphate siRNAs into leg muscle in 25 μl volume; (2) Bleed the mouse days 1, 3, or 7 following RNA injection; (3) Assay IFN a using mouse ELISA kit.

EXAMPLE 6

Materials

Reagents
Poly IC and Polymysin B were purchased from Sigma. Poly IC was further purified through extraction twice with phenol followed by ethanol precipitation. For determination of interferon alpha and beta, ELISA kits were purchased from RDI (Concord, Mass.). HEK293, NIH3T3, and MRC5 cells were cultured in DMEM media supplemented with 10% Fetus Bovine Serum and glutamine. The enolase antibody was purchased from Biogenesis (Kingston, HN). HnRNP H antibody was a generous gift from Dr. Black Lab (UCLA, CA). Cytoplasmic and nucleus extracts were prepared as described with a modification (Robb, G. G., et al., 2005). The isolated nuclei and cytoplasmic extract were mixed with Stat 60 (Tel-Test) followed by the Manufacturer's instructions to purify RNA.
siRNAs
The anti-poliovirus siRNA (siC (Gitlin, L., et al., 2002); sense sequence 5'-GCGUGU AAUGACUUCAGCGUG-3' (SEQ ID NO: 19)) and anti-HSV siRNA (sigE (Bhuyan, P. K., et al., 2004); sense sequence 5'-AATATACGAATCGTGTCT-GTA-3' (SEQ ID NO:20)). were synthesized by the oligo synthesis facility at the City of Hope (Duarte, Calif.).
T7 siRNAs
The T7 siRNAs were synthesized using the Silencer siRNA Construction kit from Ambion, Inc. according to the manufacturer's protocol. To transcribe RNA in vitro, T7 primer I (5'-TAATACGACTCACTATA-3' (SEQ ID NO: 15)) was hybridized with T7 primer II which contains the antisense sequence of each transcribed RNA and the tail sequence: 5'-CCCTATAG TGAGTCGTA-3' (SEQ ID NO:16). The anti-EMCV siRNA is targeted to the sequence: 5'-GAT AGTGC-CAGGGCGGGTACT-3' (SEQ ID NO:21). The transcribed ssRNA was used as T7 RNA without hybridization. For the CIP treatment, 20 U of enzyme (NEB) was added to the siRNA after DNase and RNase T1 digestion, and further incubated at 37° C. for 1 hour. siRNAs were column purified using conditions recommended for the Silencer siRNA Construction Kit.

EXAMPLE 7

Transfection

All transfection assays were done using Lipofectamine 2000 (Invitrogen). HEK293 or NIH3T3 cells at 50 to 60 percent confluency were transfected with each siRNAs using indicated concentrations. The siRNA and lipofectamine complex was simply added on top of existing growth media.

EXAMPLE 8

Viral Challenge Assay

For anti-HSV-1 or anti-polioviral assays, 60% confluent 293 cells on plates were transfected with siRNA or ssRNA using Lipofectamine 2000 (Invitrogen). The following day (24 hours) the cells were infected with HSV-1 expressing the EGFP or Poliovirus Mahoney strain at a multiplicity of infection of 1 or 0.1, respectively. 24 hours post infection, the anti-HSV activity was measured by determining the EGFP level in the extract using a Fluorometer (Bio-Rad). To prepare the extract, the cells in the 24 well plates were mixed with 200 μl of passive lysis buffer (Promega). For the anti-poliovirus assay, the cells in each well were washed with PBS three times to remove dead cells caused by the cytotoxic effect of the virus and lysed by adding 200 μl of the lysis buffer. Total amount of protein was measured by the Bradford assay. For anti-proliferation effect of T7 RNA or poly IC, 40% of the NIH3T3 cells stably expressing EGFP gene was plated in 24 well plates on day 1. The cells were transfected with T7 RNA or poly IC and harvested on day 5. Total cell numbers were determined by measuring EGFP levels using the fluorometer. For the anti-EMCV activity assay, cells were transfected with indicated amount of each RNAs on day 2. On day 3, the cells were infected with a 0.1 MOI of EMCV. Total anti-EMCV activity was measured on day 5 or day 7. Total numbers of survived cells were determined by the level of EGFP expression in the extracts after normalization to the value of each parallel sample from the anti-proliferation activity assay.

EXAMPLE 9

Viral RNA

Influenza virus A/PR/8/34 (PR8), subtype H1N1, a kind gift from Dr. Peter Palese, Mount Sinai School of Medicine, was grown for 48 hours in 10-day-embryonated chicken eggs (Charles River laboratories, MA) at 37° C. 48 hours after virus inoculation, the allantoic fluid was harvested and was centrifuged at 1300 rpm for 10 min. The supernatant was then mixed with 25% sucrose in 0.1 M Tris (pH8.0) and ultracentrifuged at 25,000 rpm for 2 hours using SW28. Following centrifugation, Trizol (Invitrogen) was added to the pellet and RNA purification was performed according to the manufacturer's instructions.

EXAMPLE 10

RT-PCR

Total RNA was purified using Stat60 and treated with 2 U of DNase (Promega) per ug of RNA for 20 min at 37° C. To detect Tlr3, Tlr7 and β-actin mRNA using reverse transcriptase (RT) and PCR, first strand cDNA synthesis was performed at 37° C. for 1 hour in a 30 μl reaction mixture containing 2 μg of total cellular RNA, 2 μmol of gene-specific primer (50 ng of random primers (invitrogen)), 0.5 mM each of DATP, dCTP, dTTP and dGTP, 3 mM $MgCl_2$, 50 mM Tris-HCl (pH 8.3), 75 mM KCl, 20 mM DTT, 5 U RNasin RNase inhibitor (Promega) and 200 U M-MLV Reverse Transcriptase (Invitrogen). Reverse primers used for the PCR reaction (see below) were used as gene-specific primers for first strand synthesis of Tlr3 and Tlr7. Aliquots (5 μl) of the cDNA reaction mixture were used to amplify Tlr3, Tlr7 and β-actin sequences separately. The PCR reaction mixtures included 50 mM KCl, 10 mM Tris-HCl (pH 8.3 at 25° C.), 1.5 mM $Mg(OAc)_2$, 0.2 mM each of dATP, dCTP, dTTP and dGTP, 15 pmol each of forward and reverse primers, and 2.5 U of Taq DNA polymerase (Eppendorf). Sequences of forward and reverse Tlr3 primers were 5'-AGATACAACG-TAGCTGACTGCAGCCATTTG-3' (SEQ ID NO:22) and 5'-CTTCACTTCGCAACGCAAGGATTTTATTTT-3' (SEQ ID NO:23). Sequences of forward and reverse Tlr7 primers were 5'-CATTCCCACTAACACCACCAATCT TACCCT-3' (SEQ ID NO:24) and 5'-ATCCTGTGGTATCTCCA-GAAGTTGGTTTCC-3' (SEQ ID NO:25). Sequences of forward and reverse β-actin primers were 5'-ACCAACTGG-GACGA CATGGAGAAGATCTGG-3' (SEQ ID NO:26) and 5'-GCTGGGGTGTTGAAGGTCTCAAA CATGATC-3' (SEQ ID NO:27). Thermal cycling reactions were conducted at 95° C. for 30 seconds, 58° C. for 30 seconds and 72° C. for 1 minute. Aliquots were removed from the PCR reaction mixtures during the exponential phase of amplification after 25 (β-actin) and 35 cycles (Tlr3 and Tlr7). Samples were resolved using 2% agarose gel electrophoresis. The same procedure was used for RT-PCR of other genes using each pair of primers (for Stat 1, Ifi44, Tgtp, TNFaip3, Gadd4alpha).

EXAMPLE 11

Functional Inhibition Assay for TLR3

The procedure was followed as previously described (Matsumoto, M., et al., 2002). Anti-TLR2 and TLR3 antibodies were purchased from eBioscience (San Diego, Calif.). Briefly, MRC-5 cells in 24 well pates ($1\times10^5$) were preincubated with 20 μg/ml of anti-TLR2 or anti-TLR3 antibody for 1 hour at 37° C. The cells were transfected with either 5 nM of T7 RNA or 500 ng of poly IC. The next day, interferon beta levels in the media was determined by ELISA (RDI).

EXAMPLE 12

Microarray

Mouse oligonucleotides were purchased from Operon Technologies Inc. (Alameda, Calif.) and Sigma-Genosys (The Woodlands, Tex.), and were inkjet-printed by Agilent Technologies (Palo Alto, Calif.). The 16K oligo array includes 13,536 Operon designed and synthesized probes (70 mer), and 2,304 Compugen Ltd. (Jamesburg, N.J.) designed and Sigma-Genosys synthesized probes (65 mer). The aminoallyl method was used for the preparation of fluorescently labeled target samples. Briefly, both first and second strand cDNAs were synthesized by incubating 3 μg of total RNA with the T7 promoter primer (5'-GGCCAGTGAA TTG-TAATACGACTCACTATAGGGAGGCGG-(dT)$_{24}$-3' (SEQ ID NO:28)) (Qiagen Inc., Valencia, Calif.) followed by using SuperScript II (Invitrogen Life Technologies, Carlsbad, Calif.). Aminoallyl-UTP (aaUTP) labeled antisense RNA (aRNA) was synthesized by adding reagents to the 15 μl of cDNA template in the following order: 4 μl of 75 mM ATP solution; 4 μl of 75 mM CTP solution; 4 μl of 75 mM GTP solution; 2 μl of 75 mM UTP solution; 4 μl of 10× reaction buffer; 3 μl of 50 mM aaUTP (Ambion, Austin, Tex.); and 4 μl of MEGAscript T7 enzyme mix (Ambion). The coupling reaction was performed by mixing 10 μg of aRNA with 2 μl of 0.5 M sodium bicarbonate, pH 9.5, along with 10 μl of mono-Cy3 or mono-Cy5 solution (PerkinElmer, Inc.; Boston, Mass.), and adjusting the final volume to 20 μl/reaction. Three μg of each labeled aRNA target was hybridized after being fragmented by mixing with fragmentation buffer (Agilent Technologies). After hybridization and washing, oligo arrays were scanned by the Agilent Scanner G2505A (Agilent Technologies). Genes that were saturated, non-uniform, or not significantly above background (below 2.6× standard deviation of background) in either channel were removed. The remaining values were used for the analysis.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Ackermann, E. J., et al. Antisense modulation of novel anti-apoptotic bcl-2-related proteins. U.S. Pat. No. 6,001,992 (1999).

Agrawal, S., et al. Method of down-regulating gene expression. U.S. Pat. No. 6,645,943 (2003).

Akhtar, S. (ed.). Delivery Strategies for Antisense Oligonucleotide Therapeutics, CRC Press, Boca Raton, Fla. (1995).

Akhtar, S. and Juliano, R. L. Cellular uptake and intracellular fate of antisense oligonucleotides. Trends Cell Biol, 2, 139 (1992).

Alexopoulou, L., et al. Recognition of double-stranded RNA and activation of NF-kappaB by Toll-like receptor 3. *Nature* 413, 732-8 (2001).

Andino, R. RNAi puts a lid on virus replication. *Nat. Biotechnol.* 21, 629-630 (2003).

Beigelman et al. Novel compositions for the delivery of negatively charged molecules. PCT international published application No. WO 99/05094 (1999).

Beutler, B. Inferences, questions and possibilities in Toll-like receptor signalling. *Nature* 430, 257-63 (2004a).

Beutler, B. Innate immunity: an overview. *Mol Immunol* 40, 845-59 (2004b).

Boehme, K. W. and Compton, T. Innate sensing of viruses by toll-like receptors. *J Virol* 78, 7867-73 (2004).

Bridge, A. J., et al., Induction of an interferon response by RNAi vectors in mammalian cells. *Nature,* 34(3), 263-264 (2003).

Capodici, J., et al. Inhibition of HIV-1 infection by small interfering RNA-mediated RNA interference. *J. Immunol.* 169, 5196-5201 (2002).

Chou, M. Y., et al. hnRNP H is a component of a splicing enhancer complex that activates a c-src alternative exon in neuronal cells. *Mol Cell Biol* 19, 69-77 (1999).

Der, S. D., et al. A double-stranded RNA-activated protein kinase-dependent pathway mediating stress-induced apoptosis. *Proc Natl Acad Sci USA* 94, 3279-83 (1997).

Diebold, S. S., et al. Innate antiviral responses by means of TLR7-mediated recognition of single-stranded RNA. *Science* 303, 1529-31 (2004).

Dolken, G., et al. Immunofluorescent localization of glycogenolytic and glycolytic enzyme proteins and of malate dehydrogenase isozymes in cross-striated skeletal muscle and heart of the rabbit. *Histochemistry* 43, 113-21 (1975).

Donze, O. and Picard, D. RNA interference in mammalian cells using siRNAs synthesized with T7 RNA polymerase. *Nucleic Acids Res.* 30, e46 (2002).

Draper et al. Method and reagent for inhibiting viral replication. PCT international published application No. WO 93/23569 (1993).

Elbashir, S. M., et al. Duplexes of 21-nucleotide RNAs mediate RNA interference in cultured mammalian cells. *Nature* 411, 494-498 (2001).

Elliott, G. and O'Hare, P. Live-cell analysis of a green fluorescent protein-tagged herpes simplex virus infection. *J. Virol.* 73, 4110-4119 (1999).

Fire, A., et al. Genetic inhibition by double-stranded RNA. U.S. Pat. No. 6,506,559 (2003).

Geiss, G. et al. A comprehensive view of regulation of gene expression by double-stranded RNA-mediated cell signaling. *J Biol Chem* 276, 30178-82 (2001).

Gu, M. and Lima, C. D. Processing the message: structural insights into capping and decapping mRNA. *Curr Opin Struct Biol* 15, 99-106 (2005).

Hannon, G. J. RNA interference. *Nature* 418, 244-251 (2002).

Heil, F. et al. Species-specific recognition of single-stranded RNA via toll-like receptor 7 and 8. *Science* 303, 1526-9 (2004).

Honda, A., et al. Identification of the 5' terminal structure of influenza virus genome RNA by a newly developed enzymatic method. *Virus Res.* 55, 199-206 (1998).

Hornung, V. et al. Sequence-specific potent induction of IFN-alpha by short interfering RNA in plasmacytoid dendritic cells through TLR7. *Nat Med* 11, 263-70 (2005).

Kapadia, S. B., et al. Interference of hepatitis C virus RNA replication by short interfering RNAs. *Proc. Natl. Acad. Sci. USA* 100, 2014-2018 (2003).

Kariko, K., et al. mRNA is an endogenous ligand for Toll-like receptor 3. *J Biol Chem* 279, 12542-50 (2004).

Kim, D. H. and Rossi, J. J. Coupling of RNAi-mediated target downregulation with gene replacement. *Antisense Nucleic Acid Drug Dev.* 13, 151-155 (2003).

Kim, D. H. et al. Interferon induction by siRNAs and ssRNAs synthesized by phage polymerase. *Nat Biotechnol* 22, 321-5 (2004).

Kim, D. H. et al. Synthetic dsRNA Dicer substrates enhance RNAi potency and efficacy. *Nat Biotechnol* 23, 222-6 (2005).

Klimuk, et al. Liposomal compositions for the delivery of nucleic acid catalysts. PCT international published application No. WO 99/04819 (1999).

Lamb, R. A. & Choppin, P. W. The gene structure and replication of influenza virus. *Annu Rev Biochem* 52, 467-506 (1983).

Lund, J. M. et al. Recognition of single-stranded RNA viruses by Toll-like receptor 7. *Proc Natl Acad Sci USA* 101, 5598-603 (2004).

Malmgaard, L. Induction and regulation of IFNs during viral infections. *J Interferon Cytokine Res* 24, 439-54 (2004).

Matsumoto, M., et al. Establishment of a monoclonal antibody against human Toll-like receptor 3 that blocks double-stranded RNA-mediated signaling. *Biochem Biophys Res Commun* 293, 1364-9 (2002).

Marcus, P. I., *Interferon,* 3 (ed. Gresser, I.) 115-180 (Academic Press, London, 1983).

Montgomery, M. K. RNA Interference, Editing, and Modification: Methods and Protocols. *Methods in Molecular Biology,* 265, 3-21, (2004).

Samuel, C. E. Antiviral actions of interferons. *Clin. Microbiol. Rev.* 14, 778-809 (2001).

Samuel, C. E. Knockdown by RNAi-proceed with caution. *Nature Biotechnology,* 22(3), 280-82 (2004).

Sledz, C. A., et al. Activation of the interferon system by short-interfering RNAs. *Nature Cell Biology,* 5(9), 834-39 (2003).

Sohail, M., et al. A simple and cost-effective method for producing small interfering RNAs with high efficacy. *Nucleic Acids Res.* 31, e38 (2003).

Stewart, W. E., II., *The Interferon System* (Springer, N.Y., 1979).

Stojdl, D. F. et al. Exploiting tumor-specific defects in the interferon pathway with a previously unknown oncolytic virus. *Nat. Med.* 6, 821-825 (2000).

Sullivan et al. Method and reagent for treatment of animal diseases. PCT international published application No. WO 94/02595 (1994).

Thompson, J. et al. Nucleic acid molecules with novel chemical compositions capable of modulating gene expression. U.S. Pat. No. 6,673,611 (2004).

Wang, L. et al. Mapping oligonucleotides of Rous sarcoma virus RNA that segregate with polymerase and group-specific antigen markers in recombinants. *Proc. Natl. Acad. Sci. USA* 73, 3952-3956 (1976).

Wei, C. and Moss, B. 5'-Terminal capping of RNA by guanylyltransferase from HeLa cell nuclei. *Proc Natl Acad Sci USA* 74, 3758-61 (1977).

What is claimed is:

1. A method of inducing an anti-viral response in a cell, comprising introducing into a cell an effective amount of a siRNA molecule, wherein the siRNA molecule is double stranded, wherein the siRNA molecule has a 5'-triphosphate on each strand, wherein the siRNA molecule is targeted to a viral gene, wherein the siRNA molecule induces interferon which mediates an anti-viral response and wherein the siRNA molecule reduces expression of the targeted viral gene.

2. The method of claim 1, wherein each strand of the siRNA molecule is produced in vitro by a phage polymerase.

3. The method of claim 2, wherein the phage polymerase is T7 RNA polymerase.

\* \* \* \* \*

SEQUENCE LISTING

```
<160> NUMBER OF SEQ ID NOS: 28

<210> SEQ ID NO 1
<211> LENGTH: 120
<212> TYPE: DNA
<213> ORGANISM: Encephalomyocarditis virus

<400> SEQUENCE: 1
```
ttgaaagccg ggggtgggag atccggattg ccagtctact cgatatcgca ggctgggtcc      60
gtgactaccc actcctactt tcaacgtgaa ggctacgata gtgccagggc gggtactgcc     120

<210> SEQ ID NO 2
<211> LENGTH: 21
<212> TYPE: RNA
<213> ORGANISM: Artificial
<220> FEATURE:
<223> OTHER INFORMATION: siRNA

<400> SEQUENCE: 2
gcugacccug aaguucaucu u                                                21

<210> SEQ ID NO 3
<211> LENGTH: 21
<212> TYPE: RNA
<213> ORGANISM: Artificial
<220> FEATURE:
<223> OTHER INFORMATION: siRNA

<400> SEQUENCE: 3
gaugaacuuc agggucagcu u                                                21

<210> SEQ ID NO 4
<211> LENGTH: 24
<212> TYPE: RNA
<213> ORGANISM: Artificial
<220> FEATURE:
<223> OTHER INFORMATION: siRNA

<400> SEQUENCE: 4
ggggcugacc cugaaguuca ucuu                                             24

<210> SEQ ID NO 5
<211> LENGTH: 24
<212> TYPE: RNA
<213> ORGANISM: Artificial
<220> FEATURE:
<223> OTHER INFORMATION: siRNA

<400> SEQUENCE: 5
ggggaugaac uucaggguca gcuu                                             24

<210> SEQ ID NO 6
<211> LENGTH: 24
<212> TYPE: RNA
<213> ORGANISM: Artificial
<220> FEATURE:
<223> OTHER INFORMATION: siRNA

<400> SEQUENCE: 6
ggggcugacc cugaaguuca ucaa                                             24

<210> SEQ ID NO 7
<211> LENGTH: 24
<212> TYPE: RNA
<213> ORGANISM: Artificial
<220> FEATURE:
<223> OTHER INFORMATION: siRNA

<400> SEQUENCE: 7
ggggaugaac uucaggguca gcaa                                             24

<210> SEQ ID NO 8

```
<211> LENGTH: 26
<212> TYPE: RNA
<213> ORGANISM: Artificial
<220> FEATURE:
<223> OTHER INFORMATION: siRNA

<400> SEQUENCE: 8
gggaagcuga cccugaaguu caucaa                                    26

<210> SEQ ID NO 9
<211> LENGTH: 26
<212> TYPE: RNA
<213> ORGANISM: Artificial
<220> FEATURE:
<223> OTHER INFORMATION: siRNA

<400> SEQUENCE: 9
ggggaugaac uucaggguca gcuuaa                                    26

<210> SEQ ID NO 10
<211> LENGTH: 21
<212> TYPE: DNA
<213> ORGANISM: Artificial
<220> FEATURE:
<223> OTHER INFORMATION: siRNA

<400> SEQUENCE: 10
aactggatga aggctgggta c                                         21

<210> SEQ ID NO 11
<211> LENGTH: 21
<212> TYPE: DNA
<213> ORGANISM: Artificial
<220> FEATURE:
<223> OTHER INFORMATION: siRNA

<400> SEQUENCE: 11
aatctgtaaa ccaaatgcag c                                         21

<210> SEQ ID NO 12
<211> LENGTH: 21
<212> TYPE: DNA
<213> ORGANISM: Artificial
<220> FEATURE:
<223> OTHER INFORMATION: siRNA

<400> SEQUENCE: 12
aacaagcagc gccccggctc c                                         21

<210> SEQ ID NO 13
<211> LENGTH: 21
<212> TYPE: DNA
<213> ORGANISM: Artificial
<220> FEATURE:
<223> OTHER INFORMATION: siRNA

<400> SEQUENCE: 13
aacagcagct ccttcatcac c                                         21

<210> SEQ ID NO 14
<211> LENGTH: 21
<212> TYPE: DNA
<213> ORGANISM: Artificial
<220> FEATURE:
<223> OTHER INFORMATION: siRNA

<400> SEQUENCE: 14
```

```
aaggaacggc tcatggacgt c                                              21

<210> SEQ ID NO 15
<211> LENGTH: 17
<212> TYPE: DNA
<213> ORGANISM: Artificial
<220> FEATURE:
<223> OTHER INFORMATION: T7 primer

<400> SEQUENCE: 15
taatacgact cactata                                                   17

<210> SEQ ID NO 16
<211> LENGTH: 17
<212> TYPE: DNA
<213> ORGANISM: Artificial
<220> FEATURE:
<223> OTHER INFORMATION: T7 primer

<400> SEQUENCE: 16
ccctatagtg agtcgta                                                   17

<210> SEQ ID NO 17
<211> LENGTH: 40
<212> TYPE: DNA
<213> ORGANISM: Artificial
<220> FEATURE:
<223> OTHER INFORMATION: Primer

<400> SEQUENCE: 17
ttaagctgac cctgaagttc atccctata gtgagtcgta                           40

<210> SEQ ID NO 18
<211> LENGTH: 40
<212> TYPE: DNA
<213> ORGANISM: Artificial
<220> FEATURE:
<223> OTHER INFORMATION: Primer

<400> SEQUENCE: 18
ttgatgaact tcagggtcag cttccctata gtgagtcgta                          40

<210> SEQ ID NO 19
<211> LENGTH: 21
<212> TYPE: RNA
<213> ORGANISM: Artificial
<220> FEATURE:
<223> OTHER INFORMATION: siRNA

<400> SEQUENCE: 19
gcguguaaug acuucagcgu g                                              21

<210> SEQ ID NO 20
<211> LENGTH: 21
<212> TYPE: DNA
<213> ORGANISM: Artificial
<220> FEATURE:
<223> OTHER INFORMATION: siRNA

<400> SEQUENCE: 20
aatatacgaa tcgtgtctgt a                                              21

<210> SEQ ID NO 21
<211> LENGTH: 21
<212> TYPE: DNA
```

```
<213> ORGANISM: Artificial
<220> FEATURE:
<223> OTHER INFORMATION: siRNA target

<400> SEQUENCE: 21
gatagtgcca gggcgggtac t                                              21

<210> SEQ ID NO 22
<211> LENGTH: 30
<212> TYPE: DNA
<213> ORGANISM: Artificial
<220> FEATURE:
<223> OTHER INFORMATION: Tlr3 primer

<400> SEQUENCE: 22
agatacaacg tagctgactg cagccatttg                                     30

<210> SEQ ID NO 23
<211> LENGTH: 30
<212> TYPE: DNA
<213> ORGANISM: Artificial
<220> FEATURE:
<223> OTHER INFORMATION: Tlr3 primer

<400> SEQUENCE: 23
cttcacttcg caacgcaagg attttatttt                                     30

<210> SEQ ID NO 24
<211> LENGTH: 30
<212> TYPE: DNA
<213> ORGANISM: Artificial
<220> FEATURE:
<223> OTHER INFORMATION: Tlr7 primer

<400> SEQUENCE: 24
cattcccact aacaccacca atcttaccct                                     30

<210> SEQ ID NO 25
<211> LENGTH: 30
<212> TYPE: DNA
<213> ORGANISM: Artificial
<220> FEATURE:
<223> OTHER INFORMATION: Tlr7 primer

<400> SEQUENCE: 25
atcctgtggt atctccagaa gttggtttcc                                     30

<210> SEQ ID NO 26
<211> LENGTH: 30
<212> TYPE: DNA
<213> ORGANISM: Artificial
<220> FEATURE:
<223> OTHER INFORMATION: Beta-actin primer

<400> SEQUENCE: 26
accaactggg acgacatgga gaagatctgg                                     30

<210> SEQ ID NO 27
<211> LENGTH: 30
<212> TYPE: DNA
<213> ORGANISM: Artificial
<220> FEATURE:
<223> OTHER INFORMATION: Beta-actin primer

<400> SEQUENCE: 27
gctggggtgt tgaaggtctc aaacatgatc                                     30
```

```
<210> SEQ ID NO 28
<211> LENGTH: 63
<212> TYPE: DNA
<213> ORGANISM: Artificial
<220> FEATURE:
<223> OTHER INFORMATION: T7 promoter primer

<400> SEQUENCE: 28
ggccagtgaa ttgtaatacg actcactata gggaggcggt ttttttttt ttttttttt      60 ttt                                                                  63
```